(12) United States Patent
Gordon et al.

(10) Patent No.: US 11,746,386 B2
(45) Date of Patent: *Sep. 5, 2023

(54) ASSAYS AND METHODS FOR SELECTING A TREATMENT REGIMEN FOR A SUBJECT WITH LEUKEMIA

(71) Applicants: Celator Pharmaceuticals, Inc., Palo Alto, CA (US); Oregon Health & Science University, Portland, OR (US)

(72) Inventors: Max Gordon, Portland, OR (US); Paul Tardi, Surrey (CA); Jeffrey Tyner, Portland, OR (US); Lawrence Mayer, North Vancouver (CA)

(73) Assignees: CELATOR PHARMACEUTICALS, INC., Palo Alto, CA (US); OREGON HEALTH & SCIENCE UNIVERSITY, Portland, OR (US)

(*) Notice: Subject to any disclaimer, the term of this patent is extended or adjusted under 35 U.S.C. 154(b) by 15 days.

This patent is subject to a terminal disclaimer.

(21) Appl. No.: 17/173,677

(22) Filed: Feb. 11, 2021

(65) Prior Publication Data

US 2021/0246512 A1 Aug. 12, 2021

Related U.S. Application Data

(63) Continuation of application No. 15/774,978, filed as application No. PCT/US2016/061444 on Nov. 10, 2016, now Pat. No. 10,927,418.

(60) Provisional application No. 62/254,109, filed on Nov. 11, 2015.

(51) Int. Cl.
| | |
|---|---|
| *C12Q 1/6886* | (2018.01) |
| *A61K 31/5377* | (2006.01) |
| *A61K 31/704* | (2006.01) |
| *A61K 31/7068* | (2006.01) |
| *C12Q 1/68* | (2018.01) |
| *A61K 31/4709* | (2006.01) |
| *A61K 31/517* | (2006.01) |
| *A61K 31/496* | (2006.01) |
| *A61K 31/44* | (2006.01) |
| *A61K 31/506* | (2006.01) |
| *A61K 31/553* | (2006.01) |
| *A61P 35/02* | (2006.01) |
| *A61K 9/127* | (2006.01) |
| *A61K 31/407* | (2006.01) |

(52) U.S. Cl.
CPC ........... *C12Q 1/6886* (2013.01); *A61K 9/127* (2013.01); *A61K 31/407* (2013.01); *A61K 31/44* (2013.01); *A61K 31/4709* (2013.01); *A61K 31/496* (2013.01); *A61K 31/506* (2013.01); *A61K 31/517* (2013.01); *A61K 31/5377* (2013.01); *A61K 31/553* (2013.01); *A61K 31/704* (2013.01); *A61K 31/7068* (2013.01); *A61P 35/02* (2018.01); *C12Q 1/68* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 8,022,279 B2 | 9/2011 | Mayer et al. | |
| 8,092,828 B2 | 1/2012 | Louie | |
| 8,431,806 B2 | 4/2013 | Mayer et al. | |
| 9,993,551 B2 | 6/2018 | Lebwohl | |
| 10,028,912 B2 | 7/2018 | Cabral-Lilly | |
| 10,166,184 B2 | 1/2019 | Cabral-Lilly | |
| 10,927,418 B2* | 2/2021 | Gordon | C12Q 1/6886 |
| 2010/0298255 A1 | 11/2010 | Ballesteros et al. | |
| 2012/0010229 A1 | 1/2012 | MacDougall | |
| 2014/0255475 A1 | 11/2014 | Cabral-Lilly et al. | |
| 2019/0070112 A1 | 3/2019 | Cabral-Lilly | |
| 2021/0393665 A1* | 12/2021 | Cheung | A61P 35/02 |

FOREIGN PATENT DOCUMENTS

| | | |
|---|---|---|
| JP | 2018-535975 A | 12/2018 |
| WO | WO 2008/111441 A1 | 9/2008 |
| WO | WO-2014/087018 | 6/2014 |

OTHER PUBLICATIONS

Breems et al., "Prognostic Index for Adult Patients With Acute Myeloid Leukemia in First Relapse," Journal of Clinical Oncology (2005) 23(9):1969-1978.
Communication pursuant to Article 94(3) EPC for EP 16 865 052.1, dated Apr. 29, 2020, 9 pages.
Cortes et al., "Phase II, multicenter, randomized trial of CPX-351 (cytarabine:daunorubicin) liposome injection versus intensive salvage therapy in adults with first relapse AML," Cancer (2015) 121(2):234-242.
Döhner et al., "Diagnosis and management of acute myeloid leukemia in adults: recommendations from an international expert panel, on behalf of the European LeukemiaNet," (2010) 23 pages, Retrieved from the Internet: URL:http://www.bloodjournal.org/content/bloodjournal/115/3/453.full.pdf [retrieved on May 10, 2019].
Döhner et al., "Review Article Diagnosis and management of AML in adults: 2017 ELN recommendations from an international expert panel," (2016) Retrieved from the Internet: URL:http://www.bloodjournal.org/content/bloodjournal/129/4/424.full.pdf [retrieved on May 10, 2019].
Edwards et al., "Effective Combination of CPX-351 with FLT3 Inhibitors in AML Blasts Harboring the FLT3-ITD Mutation," Blood (2016) 128:5124, 6 pages.
Feldman et al., "First-in-man study of CPX-351: a liposomal carrier containing cytarabine and daunorubicin in a fixed 5:1 molar ratio for the treatment of relapsed and refractory acute myeloid leukemia," J Clin Oncol (2011) 29:979-985.

(Continued)

Primary Examiner — My-Chau T. Tran
(74) Attorney, Agent, or Firm — Morgan, Lewis & Bockius LLP

(57) ABSTRACT

Diagnostic methods for identifying cancer bearing subjects appropriate for treatment with CPX-351 include genetic and ex vivo testing of cells from a candidate subject. Combination treatment with CPX-351 and FLT-3 inhibitors improve CPX-351 uptake and toxicity.

8 Claims, 24 Drawing Sheets

(56) References Cited

OTHER PUBLICATIONS

Gordon et al., "Abstract 287: CPX-351 cytotoxicity against fresh AML blasts is increased for FLT3-ITD+ cells and correlates with drug uptake and clinical outcomes," Cancer Res (2016) 76(14 Suppl):Abstract nr 287.
Gordon et al., "CPX-351 exhibits potent and direct ex vivo cytotoxicity against AML blasts with enhanced efficacy for cells harboring the FLT3-ITD mutation", 2017, Leukemia Research, vol. 53, pp. 39-49.
Im et al., "DNMT3A and IDH mutations in acute myeloid leukemia and other myeloid malignancies: associations with prognosis and potential treatment strategies", 2014, Leukemia, 28(9), pp. 1774-1783.
Kampa-Schittenhelm et al., "Quizartinib (AC220) is a potent second generation class 111 tyrosine kinase inhibitor that displays a distinct inhibition profile against mutant-FLT3, -PDGFRA and -KIT isoforms", 2013, Molecular Cancer, 12(19), pp. 1-15 (https://doi.org/10.1186/1476-4598-12-19).
Kottaridis et al., "The presence of a FLT3 internal tandem duplication in patients with acute myeloid leukemia (AML) adds important prognostic information to cytogenetic risk group and response to the first cycle of chemotherapy: analysis of 854 patients from the United Kingdom Medical Research Council AML 10 and 12 trials," Blood (2001) 98(6):1752-1759.
Lancet et al., "CPX-351 Treatment of Previously Untreated Older AML Patients With High Risk AML Markedly Increases the Response Rate Over 7+3 in Patients with FLT3 Mutations," Multilearning Group Inc., Jun. 11, 2016, 3 pages.
Lancet et al., "Phase 2 trial of CPX-351, a fixed 5:1 molar ratio of cytarabine/daunorubicin, vs cytarabine/daunorubicin in older adults with untreated AML," Blood (2014) 123(21):3239-3246.
Levis et al., "In vitro studies of a FLT3 inhibitor combined with chemotherapy: sequence of administration is important to achieve synergistic cytotoxic effects," Blood (2004) 104(4):1145-1150.
Motyckova and Stone, "Treatment of Elderly Acute Myeloid Leukemia Patients," Current Treatment Options in Oncology (2011) 12:341-353.
O'Donnell et al., "Acute Myeloid Leukemia Clinical Practice Guidelines in Oncology," Natl Compr Canc Netw. (2012) 10(8):984-1021.
Sasine et al., "Emerging strategies for high-risk and relapsed/refractory acute myeloid leukemia: novel agents and approaches currently in clinical trials," Blood Rev (2014) 29:1-27.
Supplementary European Search Report for EP 16865052.1, dated May 20, 2019, 10 pages.
Thiede et al., "Analysis of FLT3-activating mutations in 979 patients with acute myelogenous leukemia: association with FAB subtypes and identification of subgroups with poor prognosis," Blood (2002) 99(12):4326-4335.
Tyner et al., "Evaluation of CPX-351 (cytarabine:daunorubicin) Liposome Injection. Anti-Leukemic Activity Against Primary Patient Leukemia Cells," Ash Annual Meeting Abstracts (2010) 116(21):2886.
Yan et al., "Exome sequencing identifies somatic mutations of DNA methyltransferase gene DNMT3A in acute monocytic leukemia", 2011, Nature Genetics, 43(4), pp. 309-315.
Yang et al., "DNMT3A in haematological malignancies", 2015, Nature Reviews Cancer, 15(3), pp. 152-165.
Stone et al., "Phase IB study of the FLT3 kinase inhibitor midostaurin with chemotherapy in younger newly diagnosed adult patients with acute myeloid leukemia," Leukemia (2012) 26:2061-2068.
Stone et al., "The Multi-Kinase Inhibitor Midostaurin (M) Prolongs Survival Compared with Placebo (P) in Combination with Daunorubicin (D)/Cytarabine KC) Induction (ind), High-Dose C Consolidation (consol), and As Maintenance (maint) Therapy in Newly Diagnosed Acute Myeloid Leukemia (AML) Patients (pts) Age 18-60 with FLT3 Mutations (muts): An International Prospective Randomized (rand) P-Controlled Double-Blind Trial (CALGB 10603/RATIFY [Alliance])," Blood (2015) 126(23):6, 8 pages.
Döhner, H. et al., "Diagnosis and management of acute myeloid leukemia in adults: recommendations from an international expert panel, on behalf of the European LeukemiaNet," Blood, Jan. 2010, 115(3):453-474.
Eriksson, A. et al., "The novel tyrosine kinase inhibitor AKN-028 has significant antileukemic activity in cell lines and primary cultures of acute myeloid leukemia," Blood Cancer Journal, 2012, 2, e81, pp. 1-9.
Nih, U.S. National Library of Medicine, ClinicalTrials.gov, "A Study of CPX-351 (Vyxeos™) With Quizartinib for the Treatment of FLT3-ITD Mutation-Positive Acute Myeloid Leukemia," NCT04209725, https://clinicaltrials.gov/ct2/show/NCT04209725, 10 pages.
Nih, U.S. National Library of Medicine, ClinicalTrials.gov, "Induction Therapy for Patients With FLT3 Mutated Acute Myeloid Leukemia," NCT04982354, https://clinicaltrials.gov/ct2/show/NCT04982354, 8 pages.
Sasine, J. et al., "Emerging strategies for high-risk and relapsed/refractory acute myeloid leukemia: Novel agents and approaches currently in clinical trials," Blood Reviews, 2015, 29:1-9.

\* cited by examiner

|  |  |  |  |  |  |  |
|---|---|---|---|---|---|---|
| \multicolumn{6}{c}{CPX-351} | |
| 500 | 200 | 80 | 32 | 12.8 | 5.12 | ME-1 |
| 500 | 200 | 80 | 32 | 12.8 | 5.12 | MOLM-13 |
| 500 | 200 | 80 | 32 | 12.8 | 5.12 | MOLM-14 |
| 100 | 40 | 16 | 6.4 | 2.56 | 1.024 | GDM-1 |
| 10000 | 2500 | 625 | 156 | 39.1 | 9.77 | HL-60 |
| 10000 | 2500 | 625 | 156 | 39.1 | 9.77 | U-937 |
| 100 | 40 | 16 | 6.4 | 2.56 | 1.024 | KG-1 |

Quizartinib

| | | | | | | |
|---|---|---|---|---|---|---|
| ME-1 | 0.0512 | 0.128 | 0.32 | 0.8 | 2 | 5 |
| MOLM-13 | 0.0512 | 0.128 | 0.32 | 0.8 | 2 | 5 |
| MOLM-14 | 0.0512 | 0.128 | 0.32 | 0.8 | 2 | 5 |
| HL-60 | 9.77 | 39.1 | 156 | 625 | 2500 | 10000 |
| U-937 | 9.77 | 39.1 | 156 | 625 | 2500 | 10000 |
| KG-1 | 9.77 | 39.1 | 156 | 625 | 2500 | 10000 |

Midostaurin

| | | | | | | |
|---|---|---|---|---|---|---|
| ME-1 | 0.977 | 3.90 | 15.6 | 62.5 | 250 | 1000 |
| MOLM-13 | 0.0977 | 0.391 | 1.56 | 6.25 | 25 | 100 |
| MOLM-14 | 0.0977 | 0.391 | 1.56 | 6.25 | 25 | 100 |
| GDM-1 | 0.977 | 3.90 | 15.6 | 62.5 | 250 | 1000 |
| HL-60 | 9.77 | 39.1 | 156 | 625 | 2500 | 10000 |
| U-937 | 9.77 | 39.1 | 156 | 625 | 2500 | 10000 |
| KG-1 | 0.977 | 3.90 | 15.6 | 62.5 | 250 | 1000 |

ASSAYS AND METHODS FOR SELECTING A TREATMENT REGIMEN FOR A SUBJECT WITH LEUKEMIA

CROSS-REFERENCE TO RELATED APPLICATIONS

This application is a continuation of U.S. application Ser. No. 15/774,978, having an international filing date of 10 Nov. 2016, which is the national phase of PCT application PCT/US2016/061444 having an international filing date of 10 Nov. 2016, which claims benefit of U.S. provisional application No. 62/254,109 filed 11 Nov. 2015. The contents of the above patent applications are incorporated by reference herein in their entirety.

TECHNICAL FIELD

The invention is in the field of cancer diagnostics and treatment. More specifically, it concerns identification of subjects who would best benefit from treatment with a synergistic liposomal combination of daunorubicin and cytarabine.

BACKGROUND ART

CPX-351 is a nano-scale (100 nm diameter) low-cholesterol liposome formulation containing cytarabine and daunorubicin co-encapsulated at a 5:1 molar ratio (U.S. Pat. Nos. 8,022,279 and 8,431,806) shown to be optimally synergistic both ex vivo and in vivo. Dramatic improvements in efficacy over the conventional free drug combination were observed in several preclinical studies and, more importantly, CPX-351 provided increased complete remission and survival rates compared to standard of care treatment in clinical trials; one in newly diagnosed elderly acute myelogenous leukemia (AML) and the other in adult first relapse AML patients. The current treatment for AML is "standard-of-care" otherwise termed "7+3" treatment.

The present invention focuses on identifying populations of patients for whom treatment with CPX-351 as opposed to the current "standard-of-care" is beneficial and to provide analyses that take account of heterogeneity of cancers as they occur among individual patients.

The efficacy observed in clinical trials with CPX-351 are attributable to 1) elevated cytarabine:daunorubicin concentrations maintained in the circulation at a synergistic ratio for prolonged periods of time (hence avoidance of antagonistic ratios), 2) increased accumulation and persistence of CPX-351 in bone marrow, and 3) selective accumulation and cytotoxicity of intact CPX-351 liposomes by leukemia cells compared to normal cells in the bone marrow. CPX-351 has been shown to be very effective at rapidly eliminating leukemia cells from the circulation and bone marrow in a high proportion of high risk AML patients, including those who had failed to respond to "standard of care" 7+3 cytarabine:daunorubicin treatment just prior to CPX-351 therapy, as well as in advanced adult acute lymphocytic leukemia (ALL) and myelodysplastic syndrome (MDS) patients.

Short-term, ex vivo cytotoxicity assays using freshly isolated leukemic cells from patients with hematologic malignancies can sometimes be useful to provide an indication of the spectrum of activity of therapeutic agents against hematological malignancies. In this context, the present inventors have established a process of collecting and purifying circulating blast cells from freshly obtained blood samples in patients with a wide array of hematological malignancies, including acute myelogenous leukemia (AML), ALL, chronic lymphocytic leukemia (CLL), chronic myeloid leukemia (CML), myeloproliferative neoplasms (MPNs) and lymphomas for the purpose of evaluating anti-neoplastic activity in individual patients. Applicants have also established a profile of anti-proliferative/cytotoxic activity for many new investigational agents, categorized based on the type of hematological malignancy and also specific phenotypic profiles of patient sub-types within such malignancies. Fifty and ninety percent growth inhibition concentrations ($IC_{50}$ and $IC_{90}$, respectively) in such assays are used to predict whether treatment sensitivities reflect drug concentrations that are acceptable and what proportion of a given class of patients are sufficiently sensitive to warrant testing in a clinical trial setting. Thus, correlations between drug sensitivity and sub-population phenotypes identify biomarkers that inform patient selection.

However, historically, evaluation of nano-particulate (e.g., liposome and nanoparticle) drug formulations ex vivo for cytotoxicity against cancer cells has typically not been done due to the fact that such formulations are typically designed so as to act as an in situ drug infusion reservoir where the vehicles accumulate preferentially in sites of cancer growth and once there, slowly release free drug, which is then taken up by the cancer cells. Since drug release rates ex vivo are normally much slower than observed in vivo, the cytotoxic potencies of encapsulated anticancer drugs are often orders of magnitude lower ex vivo than observed for their free drug counterparts, and ex vivo testing has been less reliable in predicting in vivo success.

Uniquely, in the case of CPX-351, applicants have demonstrated that human leukemia cells take up cytarabine and daunorubicin in liposome-encapsulated form both ex vivo and in vivo via an energy dependent mechanism. Once taken up into vacuoles within the cytoplasm, the liposomes generate bioavailable drug, leading to cell killing activity. This not only ensures delivery of the synergistic 5:1 molar ratio of cytarabine:daunorubicin but also leads to CPX-351 ex vivo cytotoxic potencies (based on $IC_{50}$ values) that are comparable, and in some cases more potent, than those for the free drugs, as shown herein.

Pilot investigations into the ex vivo cytotoxicity of CPX-351 against fresh leukemia blasts from a variety of leukemia conditions yielded $IC_{50}$ values as low as 50 nM cytarabine: 10 nM daunorubicin under incubation conditions where drug release from the liposomes in the medium was non-detectable (Tyner, J., et al., *Blood* (2010) 116: Abstract 2886). This confirmed that the direct anti-leukemic activity of intact CPX-351 liposomes documented previously with leukemia cell lines was relevant for blasts freshly obtained from patients. This also allows the dissection of how genotypic/phenotypic cellular features influence the sensitivity of blasts to CPX-351 independent of PK contributions.

Consequently, in contrast to the performance of nanoparticulate compositions generally, examination of ex vivo CPX-351 cytotoxicity against and/or CPX-351 uptake by fresh patient samples provides a way to predict anti-neoplastic activity of CPX-351 in individual patients and population types.

The conventional, standard-of-care treatment for leukemia has been the same for over 40 years and employs anthracycline plus cytarabine sequentially in their free forms as "7+3" therapy. Though this treatment is "standard," there are side effects and/or poor prognosis in some patients. CPX-351 may offer a positive alternative in such patients. Thus, there is a need to stratify patients with blood cancers such that they can receive CPX-351 as an appropriate therapy. As CPX-351 and/or conventional treatment regimens may not be effective for each and every individual, there is a need to identify diagnostic tests, agents and/or markers that can facilitate selection of an appropriate treatment regimen for a subject with bloodborne cancers.

DISCLOSURE OF THE INVENTION

The invention, in one aspect, is based on the ex vivo assessment of CPX-351 cytotoxicity and/or uptake against a wide range of blast types freshly harvested from hematologic malignancy patients, including cells from major hematologic cancer groups such as AML and CLL as well as different disease sub-types. The results are correlated with patient outcomes following in vivo treatments.

The hematologic cancer includes acute myelogenous leukemia (AML), acute lymphocytic leukemia (ALL), chronic lymphocytic leukemia (CLL), chronic myeloid leukemia (CML), myeloproliferative neoplasms (MPNs) and lymphomas.

Thus, in this aspect, the invention is directed to a method to predict the probability that administering CPX-351 to a human subject will be effective in treating a hematologic cancer in and subject which method comprises exposing cancer cells from said subject to treatment with CPX-351 in a cell culture ex vivo; and measuring the responsiveness to said treatment of said cells;

wherein a subject whose cells show response to said treatment is identified as a subject for whom treatment with CPX-351 is likely to be effective. Responsiveness can be measured as cytotoxicity, for example, using $IC_{50}$ or $IC_{90}$ determination or by measuring CPX-351 uptake.

Subjects thus identified are administered CPX-351 in an effective amount.

In a second aspect, the invention is directed to identifying those subjects who will most benefit from substituting the more expensive CPX-351 treatment for standard-of-care thus potentially leading to regulatory approval for the use of CPX-351 for these subjects. These subjects are identified by virtue of certain genetic and phenotypic characteristics described below.

In particular embodiments, the method for identification comprises determining the presence or absence of a mutation in the Fms-like tyrosine receptor kinase 3 (FLT-3) gene in said subject, whereby a subject who exhibits a mutation in said FLT-3 gene is identified as a subject who will benefit from treatment with CPX-351 and, in some embodiments, further comprises administering an effective amount of CPX-351 to said subject and/or determining the presence or absence of a mutation in the nucleophosmin 1 (NPM-1) gene in said subject, whereby a subject who exhibits a mutation in said NPM-1 gene is identified as a subject who will benefit from treatment with CPX-351 and, in some embodiments, further comprises administering an effective amount of CPX-351 to said subject; and/or determining the presence or absence of a mutation in the CCAAT enhancer binding protein alpha (CEBPα) gene in said subject, whereby a subject who exhibits a mutation in said CEBPα gene is identified as a subject who will benefit from treatment with CPX 351 and, in some embodiments, further comprises administering an effective amount of CPX 351 to said subject.

In the case of FLT-3 mutations, the mutation may be an activating mutation for this gene, in particular, the FLT3-IDT lesion.

One or a combination of biomarkers such as those above that can be indicative of a patient (e.g., with leukemia or at risk for leukemia) suitable for a treatment regimen comprising CPX-351 includes, but is not limited to, at least one or more mutation to the FLT-3 gene, including the FLT3-ITD lesion or FLT3-TKD lesion and any combination of mutations thereof, or combination with other genetic markers such as mutations in the NPM-1 gene and/or CEBPα gene. When approved, CPX-351 can be used in the absence or presence of other anticancer treatments (e.g., radiation, surgery) for bloodborne cancer in subjects selected for carrying at least one or more biomarkers described herein. In alternative embodiments, when approved, CPX-351 can be used as a bone marrow conditioning agent for treatment of such cancers in subjects selected for carrying at least one or more biomarkers described herein.

In addition to the FLT-3, NPM-1 and CEBPα markers, other karyotypes can comprise one or two CPX-351-responsive alleles according to the European LeukemiaNet (ELN) Guidelines described in Example 1 below.

Thus, the invention is also directed to a method to identify a cancer-bearing subject that will benefit from treatment with CPX-351 wherein the method comprises determining the genotype of the subject according to the ELN system so as to classify the subject as favorable risk, intermediate-I, intermediate-II or adverse risk. Subjects that are intermediate-II or adverse risk are identified as likely to benefit from CPX-351 treatment, and are so treated. The ELN system is based on response to the standard 7+3 treatment and those with adverse risk do not respond well.

It should be clear that the classification according to ELN can be combined with the foregoing genetic markers to determine subjects who will benefit from treatment.

Thus, in general, the invention in the aspects set forth above relates to assays, methods, systems, and kits for selecting a treatment regimen for a subject with bloodborne cancer (e.g., leukemia) or a risk for bloodborne cancer (e.g., leukemia), treating a subject with bloodborne cancer (e.g., leukemia), and/or improving the effectiveness of a treatment regimen recommended for or administered to a subject with bloodborne cancer (e.g., leukemia) or a risk for bloodborne cancer (e.g., leukemia).

The test sample for use in the assays, methods, systems or kits described herein can be derived from a biological sample of the subject, e.g., a bone marrow, or blood sample or plasma or serum sample from the subject.

Depending upon selection of the at least one biomarker described herein, the test sample can be subjected to one or more analyses, e.g., including, but not limited to, genotyping assays, expression assays (e.g., protein and/or transcript levels), other assays capable of identifying a genotype or any combinations thereof. A plethora of such assays is known in the art and many are commercially available such as microarrays (e.g., Affymetrix®) and sequencing (e.g., Illumina).

The hematologic cancer includes acute myelogenous leukemia (AML), acute lymphocytic leukemia (ALL), chronic lymphocytic leukemia (CLL), chronic myeloid leukemia (CML), myeloproliferative neoplasms (MPNs) and lymphomas.

In another aspect, the invention is directed to a method to enhance the effectiveness of treatment with CPX-351 in a hematologic cancer-bearing subject having an activating mutation in the FLT-3 gene, which method comprises administering, in combination with CPX-351, an effective amount of an inhibitor of FLT-3. The combination can be administered at the same time or in the same composition or CPX-351 is administered first.

BRIEF DESCRIPTION OF THE DRAWINGS

FIGS. 5A and 5B respectively show uptake of cytarabine and daunorubicin from CPX-351 and FIG. 5C shows uptake of lipid.

FIG. 10A shows the nature of the diagrams that will be created based on various concentrations of these drugs as shown. FIG. 10B shows depictions of synergy according to Excess Over Bliss Additivity (EOBA) algorithm (Berenbaum, M. C., Adv. Cancer Res. (1981) 35:269-335). FIG. 10C shows the viability results for individual cell lines and various protocols of administering the combinations along with the results of the EOBA analysis.

FIG. 11A shows the positions in a multiwell plate of various combinations of drug concentrations that were subjected to the analysis. FIG. 11B shows an example of a diagram useful for plotting the results for each combination. FIGS. 11C and 11D show the results for the combinations tested.

MODES OF CARRYING OUT THE INVENTION

Figure 1A:
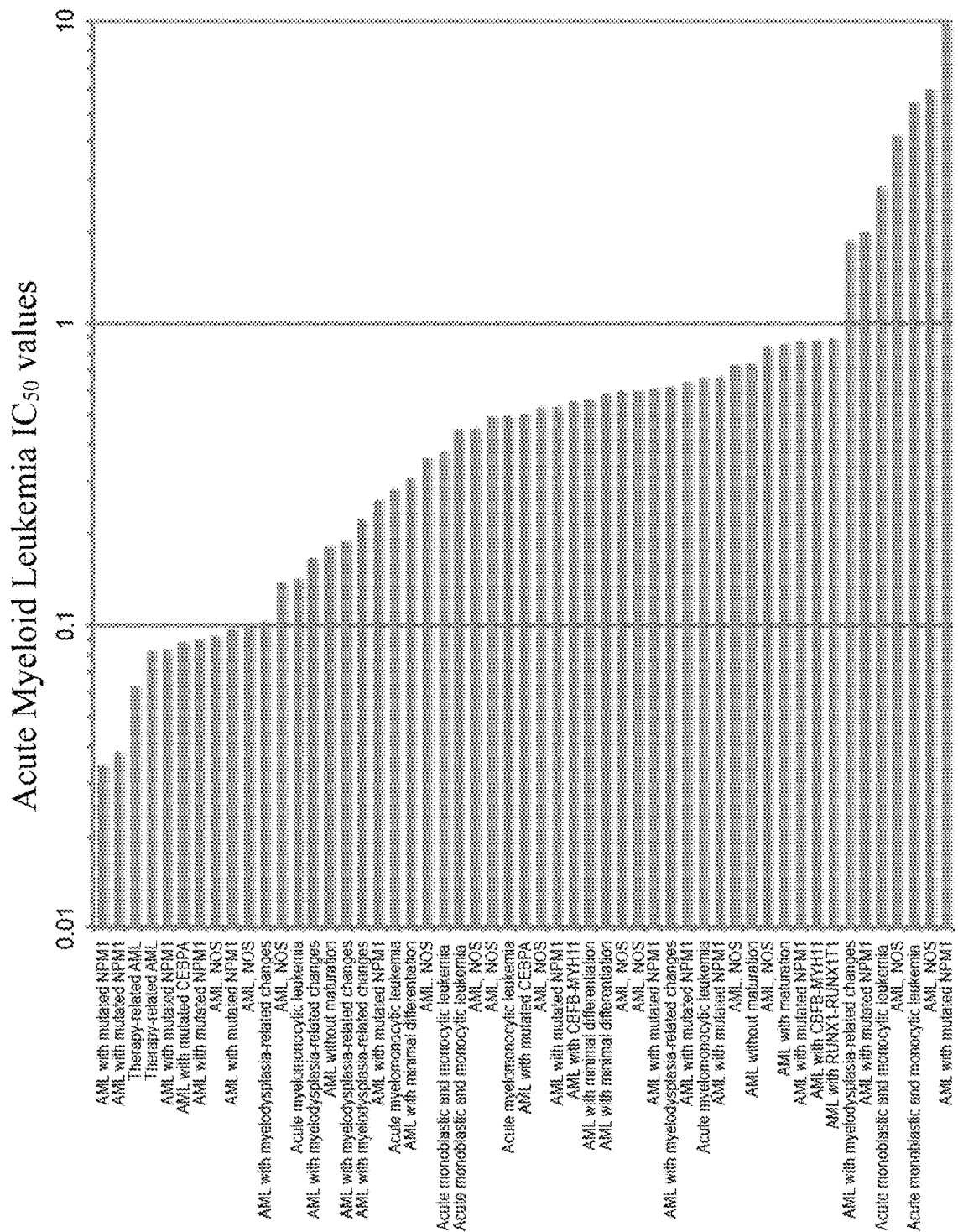
FIG. 1A is a chart showing the ex vivo sensitivity of AML patient cells to CPX-351. $IC_{50}$ values are correlated with more specific AML risk subtypes annotated on the chart. CPX-351 $IC_{50}$ values for patients in each of these risk groups are displayed.

Because blood-borne cancers are heterogeneous—i.e., not all patients with AML or other hematologic cancers have the same prognosis or basic genotype—it is important to test individual human samples in order to determine a beneficial treatment for the specific individual involved.

As noted above, in contrast to previous experience with liposome and nanoparticle drug formulations, CPX-351 is successful in being taken up by leukemic cells (in preference to normal bone marrow cells) along with the encapsulated cytarabine and daunorubicin in the administered ratio. (Lim, W. S., et al., Leuk. Res. (2010) 34:1214-1223.) This enables ex vivo testing of individual hematological cancers for the susceptibility to treatment with CPX-351. The assay may involve either or both the ability of the cells to take-up significant amounts of CPX-351 and/or cytotoxicity of CPX-351 to patient samples. This is important due to the heterogeneity of response of individual patients to treatments in general, and the advantage of ascertaining in advance whether treatment with CPX-351 will be advantageous for the particular individual. Generally, such ex vivo testing has been limited to free drugs as opposed to drugs delivered in nanoparticulate formulations since these formulations are designed to accumulate in the bloodstream and release the contents of therapeutic agents such that only the agents themselves enter the cancer cells.

Accordingly, one aspect of the invention is to provide ex vivo assays to determine whether an individual patient will successfully respond to CPX-351. Cancer cells are thus taken from a patient with a hematological cancer for ex vivo testing by contacting the cells with CPX-351 and determining cytotoxicity, for example, by determining the $IC_{50}$ or $IC_{90}$ with respect to these cells and/or measuring the uptake of the liposomal system by any convenient means. As shown hereinbelow, CPX-351 is delivered intact to leukemic cells thus providing reliability for this ex vivo testing. The ex vivo cytotoxicity of CPX-351 against fresh AML blasts and blasts from acute lymphocytic leukemia (ALL), lymphoma and myeloproliferative neoplasm patients is correlated with genotypic and phenotypic profiles as well as clinical outcomes for patients from whom the blast samples were obtained.

It has also been found that mutations in certain genes, in particular FLT-3, NPM-1 and CEBPα enhance the susceptibility to CPX-351 of a hematological cancer where the subject exhibits these mutations, and in particular in comparison to the standard 7+3 treatment. Therefore, these mutations can be used as markers for cancers that will be successfully treated in vivo using CPX-351 as opposed to the standard 7+3 regimen. The presence of these mutations can be measured directly by assaying the gene, or by assessing markers indicating the mutation by virtue of downstream expression products. For example, mutations that activate FLT-3 could be identified by enhanced FLT-3 activity in the subject or in the cancer cells. Suitable substrates for these determinations include blood, plasma, serum and saliva.

For example, in some embodiments, a suitable assay can comprise subjecting a test sample from a human subject, who is diagnosed as having leukemia or having a risk for leukemia to at least one genotyping assay adapted to determine genotypes of FLT-3 gene mutations (e.g., FLT3-ITD) and optional administration of a treatment regimen comprising an effective amount of CPX-351 to the human subject.

Similar outcomes are shown for NPM-1 gene mutations, CEBPα gene mutations and individuals whose cancers fall into intermediate-II and adverse risk categories of the ELN system.

As noted above, combinations of mutations measured in any appropriate manner can be used to improve the assay. In particular, it is known that certain karyotypes in combination with a mutation status of these genes can be used to group patients according to their response to the standard 7+3 treatment. This categorization is described by Rollig, C., et al., *J. Clin. Oncol.* (2011) 29:1-7 and published online as 10.1200/JCO.210.32.8500 on 31 May 2011. The ranking system is entitled the European LeukemiaNet (ELN) system wherein subjects with AML are classified as favorable risk, intermediate-I, intermediate-II and adverse risk. Those classified as intermediate-II or adverse risk, by definition, do not respond well to the 7+3 standard regimen. In contrast, the present applicants have found these patients to be responsive to CPX-351 in clinical trials. Therefore, identifying the cancer cells of a particular patient as representing intermediate-II or adverse risk clearly indicates the desirability of treating the patient with CPX-351. The results shown by applicants are unexpected in view of experience with the standard treatment.

In all of the foregoing cases, the identification of a suitable subject is appropriately followed by administration of CPX-351 according to the approved protocol for these trials. As a result, administration of CPX-351 can be administered in an effective amount to reduce at least one symptom associated with a hematological cancer. As noted above, the hematological cancer may be one of a number of such cancers including acute myelogenous leukemia (AML), ALL, chronic lymphocytic leukemia (CLL), chronic myeloid leukemia (CML), myeloproliferative neoplasms (MPNs) and lymphomas.

The effective amount of the CPX-351 can be administered to a selected human subject via a suitable administration route, e.g., I.V. administration, through a CPX-351 dosing regimen. Treatment protocols using CPX-351 is described in U.S. Pat. No. 8,092,828 incorporated herein by reference.

Still another aspect of the invention is the design of an enhanced system for treatment of hematological cancers in individuals with FLT-3 mutations such as ITD using a combination of CPX-351 along with an inhibitor of FLT-3. FLT-3 inhibitors are available in the art and include quizartinib, midostaurin, tandutinib, sorafenib, sunitinib, lestaurtinib, crenolanib, gilteritinib, AST-487, dovitinib and linifanib. It has been found unexpectedly, however, that the timing of administration is important: The two drugs should be administered at the same time, in some cases in the same composition, or the CPX-351 should be administered prior to the inhibitor—including administration 10-24 hours before administration of CPX-351 or at intermediate times. Prolonged exposure to the FLT-3 inhibitor prior to administration of CPX-351 has been shown to be counterproductive.

Computer systems for use in any aspects of the assays and/or methods described herein are also provided. For example, one embodiment provided herein is a computer system for obtaining data from at least one test sample obtained from at least one subject.

In some embodiments, the determination module of the computer system can be configured to analyze at least one test sample to determine the presence or absence of at least two of the conditions provided above.

In some embodiments, the determination module can further comprise a comparison module adapted to compare the data output from the determination module with reference data stored on the storage device.

In some embodiments, the storage device can be further configured to store physical information of at least one subject, for example, comprising indicators of whether a test subject carries one or more mutations to the FLT-3 gene and/or NPM-1 gene and/or CEBPα gene and/or ELN karyotypes, however measured.

The assays, methods, systems and/or kits described herein can be performed and/or used by more than one entity under direction of a single director that mandates and manages these functions. Such entities may charge for a service offered to determine the presence or absence of at least one condition described herein in a test sample of a human subject, e.g., to facilitate selection of a treatment regimen for a human subject with a hematologic cancer as an element in a method for selecting a treatment regimen for a human subject. In one example, an appropriate assay comprises (a) obtaining a test sample from a human subject diagnosed as having, or having a risk, for AML; (b) subjecting the test sample to at least one biomarker analysis (e.g., including, but not limited to, genotyping assays, expression assays (e.g., protein and/or transcript levels), other assays capable of identifying activated FLT-3 or any combinations thereof) to determine parameters of at least one biomarker described herein (e.g., but not limited to, the FLT3-ITD); (c) determining, from the parameters of the selected biomarker(s), the presence of at least one claimed condition; and (d) providing a result output (e.g., but not limited to a listing of FLT3 gene mutations) setting forth whether at least one of the claimed conditions is detected in the test sample. If at least one condition is present, the director can further select and administer a treatment regimen comprising an effective amount of CPX-351 to the human subject.

In some embodiments, one or more of the steps of the method above is performed by a non-human machine.

Citation of publications or documents herein is not intended as an admission that any of the foregoing is pertinent prior art, nor does it constitute any admission as to the contents or date of these publications or documents. All documents cited herein are hereby incorporated by reference.

EXAMPLES

The following examples are offered to illustrate but not to limit the invention.

Preparation A

CPX-351 Formulation and Simple Preparation

CPX-351 (cytarabine:daunorubicin liposomes for injection) was supplied as a sterile, pyrogen free, purple, lyophilized product in 50 mL vials. Each vial contains 100 units where 1 unit equals 1.0 mg cytarabine plus 0.44 mg daunorubicin (as base). The material was reconstituted with 19 mL of water for injection and gently swirled for 10 minutes at room temperature. Working aliquots of the reconstituted product were stored frozen for no longer than 12 months at −20° C.

For patient specimen collection and preparation; peripheral blood (PB) or bone marrow (BM) specimens were obtained prior to therapy from patents diagnosed with AML, ALL, MPN, or CLL. All specimens were obtained with informed consent on a protocol approved by the Institutional Review Board of Oregon Health & Science University. Blood or bone marrow specimens were separated on a Ficoll gradient followed by red blood cell lysis with ammonium-chloride potassium (ACK) buffer.

Example 1

Determination of Ex Vivo Cytotoxicity of CPX-351 Against Patient Leukemia Cells

Drug sensitivity testing was conducted by standard, known methods. Briefly, mononuclear cells from myeloid patient specimens were cultured in R10 (RPMI-1640 medium supplemented with 10% FBS (Atlanta Biologicals, Lawrenceville, Ga.), L-glutamine, penicillin/streptomycin (Invitrogen, Carlsbad, Calif.), and Fungizone® (Invitrogen)) supplemented with $10^{-4}$M 2-mercaptoethanol (Sigma). Cells from lymphoid leukemia samples were cultured in R20 (RPMI-1640 medium supplemented with 20% FBS (Atlanta Biologicals, Lawrenceville, Ga.), L-glutamine, penicillin/streptomycin (Invitrogen, Carlsbad, Calif.), and Fungizone® (Invitrogen)) supplemented with $10^{-4}$M 2-mercaptoethanol (Sigma) insulin-transferrin-sodium selenite (Invitrogen).

Cells were cultured in 96-well plates (50,000 cells per well) and exposed to graded concentrations of CPX-351 for 3 days at which time a tetrazolium-based MTS assay (96® AQueous One Solution Cell Proliferation Assay, Promega) was used to assess the relative numbers of viable cells in each well. Cell viability readings of cells plated in the absence of any drug were set as 100% viability and each point of the CPX-351 dose response curve were normalized to the cell viability values of this no drug condition. A third order polynomial curve fit was used to generate $IC_{50}$ values for each specimen.

Since AML is currently the target indication for CPX-351, having demonstrated promising evidence of efficacy in multiple clinical studies on cohorts of AML patients with different clinical characteristics, AML blasts from peripheral blood or bone marrow specimens from 53 AML patients were cultured with graded concentrations of CPX-351 (10:2 µM; 1:0.2 µM; 0.1:0.02 µM; 0.01:0.002 µM) or no drug for 3 days and relative numbers of viable cells were assessed with a tetrazolium-based MTS assay. The MTS values of cells cultured in the absence of drug were set at 100% and the MTS values for each dose point were normalized to the MTS values of these untreated cells. A third order polynomial curve fit was used to calculate $IC_{50}$ values for each specimen. Complete demographic and clinical data were available for 42 of these cases and are summarized in Table 1. Complete cytogenetic data for evaluation of AML risk groups were available for 40 patients, with 3, 21, 12, and 4 patients falling into favorable, intermediate-I, intermediate-II, and adverse groups, respectively, as classified using the European LeukemiaNet (ELN) guidelines.

Favorable risk includes t(8;21)(q22;q22), inv(16) (p13.1q22) or t(16;16)(p13.1q22), mutated NPM1 with normal karyotype and mutated CEBPα with normal karyotype.

Intermediate-I risk includes mutated NPM1 with FLT3-ITD and normal karyotype, wild-type NPM1 with FLT3-ITD and normal karyotype, wild-type NPM1 without FLT3-ITD and normal karyotype.

Intermediate-II risk includes t(9;11)(p22;q23) and any cytogenetics not classified as favorable or adverse.

Adverse risk includes inv(3)(q21q26.2) or t(3;3) (q21q26.2), t(6;9)(p23;q34), t(v;11)(v;q23), monosomy 5 or del(5q), monosomy 7, abnormal 17p and complex karyotype (≥3 abnormalities).

The majority of specimens were obtained from newly diagnosed patients with de novo AML (34/42; 81%), and the majority of patients received the 7+3 treatment regimen subsequent to sample acquisition (32/42; 76%). Thirty-five (35) of the AML patients on study were treated with the 7+3 regimen following acquisition of the specimen. Twenty-four (24) of these patients achieved an initial complete response, while 11 patients exhibited progressive disease. CPX-351 $IC_{50}$ values for patients exhibiting complete response or progressive disease are displayed. Proportions of basic demographic features as well as clinical parameters such as WBC count at presentation and Genetic-Cytogenetic risk stratifications were representative of the general population of AML patients.

As the data in FIG. 1A and Table 2 demonstrate, primary AML leukemia blasts were generally sensitive to CPX-351 cytotoxicity ex vivo. The $IC_{50}$ values ranged from 0.035: 0.007 µM to 9.77:1.95 µM. All but one sample (98%) showed $IC_{50}$ lower than 1/10 of human plasma CPX-351 concentration at 72 hours post administration (60:12 µM cytarabine:daunorubicin), suggesting that a clinical response could be potentially achieved with CPX-351 treatment in these patients.

Figure 1B:
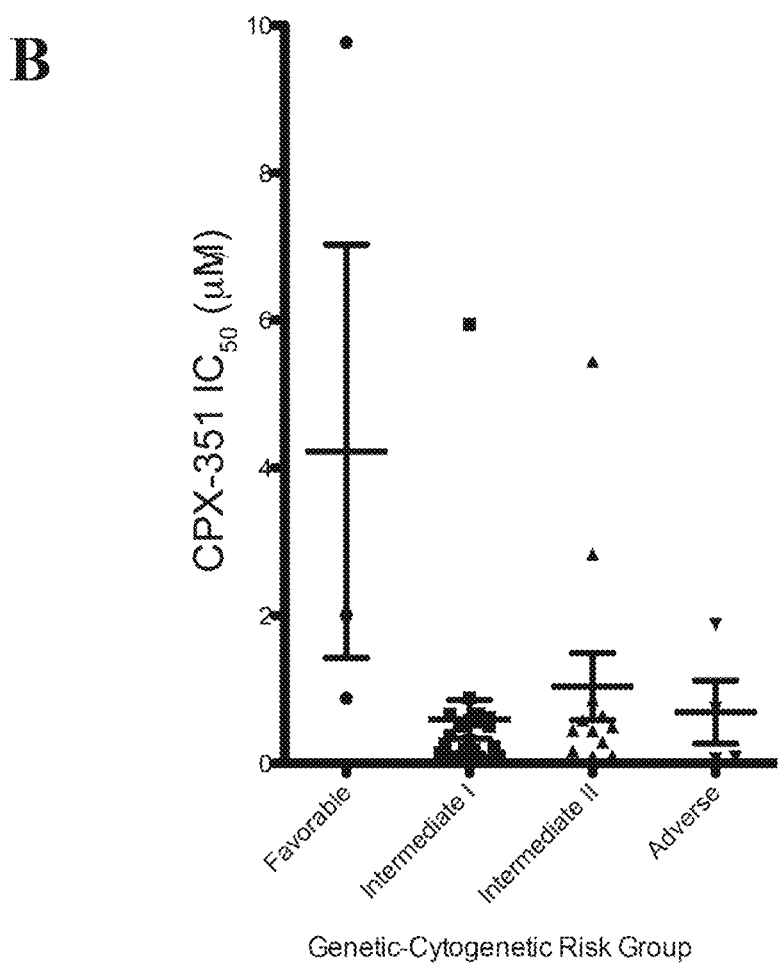
FIG. 1B shows the correlation of the risk categories with response ex vivo in terms of $IC_{50}$. As seen, while most of the subjects in intermediate-I, intermediate-II and adverse groups showed favorable $IC_{50}$ values; subjects in the favorable risk group for the most part did not. In each case, there were some outliers, pointing to the importance of individual responses.

As shown in FIG. 1B, a potent antiproliferative response to ex vivo CPX-351 treatment (low $IC_{50}$) was observed in cells carrying intermediate-II or adverse cytogenetic abnormalities, which are typically associated with worse prognosis and resistance to conventional forms of chemotherapy.

As highlighted in Table 2, a total of 17 samples were obtained from patients within the intermediate-II or adverse cytogenetics risk categories. As shown in FIG. 1B, the overall ex vivo CPX-351 response for this subgroup of patients is similar to that of intermediate-II and favorable risk patients, with no significant difference in ex vivo response to CPX-351 among the four risk groups. These ex vivo responses are well correlated with observed clinical activity of CPX-351 where the elicitation of complete responses was observed across broad, diverse subsets of AML patients irrespective of conventional risk stratification.

Figure 1C:
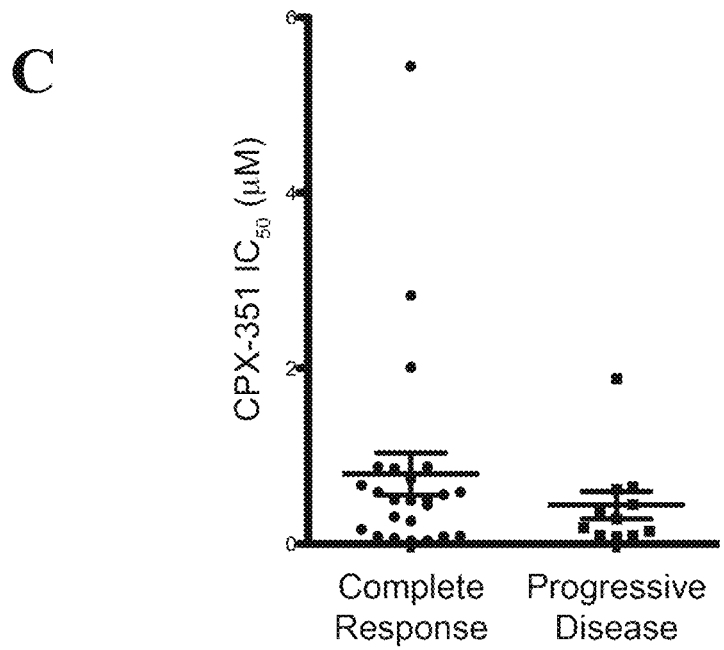
FIG. 1C shows the correlation between clinical response to the standard-of-care 7+3 regimen to responsiveness as determined $IC_{50}$ ex vivo. There appears to be little difference between groups that showed $IC_{50}$ ex vivo in the low range in their response to the 7+3 standard-of-care treatment.

Clinical response to conventional 7+3 cytarabine:daunorubicin treatment was compared to ex vivo response to CPX-351 among the 35 AML patients who received the 7+3 treatment regimen after their blasts had been collected was also assessed. Of these 35 patients, 24 achieved a complete response (CR) and 11 exhibited progressive disease (PD), as shown in FIG. 1C. The leukemia blasts from these patients showed similar sensitivity to CPX-351 cytotoxicity ex vivo regardless of whether they initially responded to 7+3.

TABLE 1

Demographic and clinical characteristics of AML patients

| Characteristics | N (%) |
|---|---|
| Age | |
| <60 years | 20 (48) |
| 60-70 years (inclusive) | 11 (26) |
| >70 years | 11 (26) |
| Gender | |
| Male | 24 (57) |
| Female | 18 (43) |
| WBC count at sample collection | |
| $<20 \times 10^9$/L | 16 (38) |
| $20\text{-}100 \times 10^9$/L (inclusive) | 18 (43) |
| $>100 \times 10^9$/L | 6 (14) |
| unknown | 2 (5) |
| Genetic-Cytogenetic risk (ELN) | |
| favorable | 3 (7) |
| intermediate-I | 22 (52) |
| intermediate-II | 13 (31) |
| Adverse | 4 (10) |
| AML type | |
| De novo | 34 (81) |
| MDS related | 6 (14) |
| Therapy related | 2 (5) |
| Post sampling treatment | |
| 7 + 3 | 32 (76) |
| Others | 10 (24) |

TABLE 2

CPX-351 Cytotoxicity, Karyotype, and Molecular Lesions of AML Patients.

| Patient ID | Cytogenetics | FLT3-ITD | NPM1 | CEBPα | CPX-351 IC$_{50}$ (uM) | Response to "7 + 3" |
|---|---|---|---|---|---|---|
| 524 | 46, XY | + | + | − | 0.035 | CR |
| 624 | 46, XX | + | + | − | 0.038 | CR |
| 202 | 47, XY, del(9)(q22), +13[18]/48, idem, +mar[2] | − | − | − | 0.063 | CR |
| 208 | 41~47, X, t(X; 7)(q28; p13), add(1)(q32), del(6)(q13q27), del(11)(q13q23), +18, −21, +mar [cp20] | − | − | − | 0.082 | PD |
| 196 | 46, XY | + | + | − | 0.083 | CR |
| 623 | 46, XY | + | − | + | 0.088 | CR |
| 170 | 46, XX, del(11)(p?13p?15)[12]/46, XX[9] | + | + | − | 0.090 | CR |
| 628 | 46, XY | + | | | 0.092 | PD |
| 45 | 46, XX | + | + | − | 0.098 | PD |
| 538 | 46, XX, del(6)(q13)[8] 46, XX, del(11)p12-14)[3]/46, XX[9] | − | − | − | 0.100 | NA |
| 510 | 46, XY, t(3; 21)(q26; q22)[17] 46, XY[3] | − | − | − | 0.103 | NA |
| 629 | 46, XX | − | − | − | 0.143 | PD |
| 520 | 47, XX, +8[19]/46, XX[1] | − | − | − | 0.167 | CR |
| 523 | 46, XY | − | − | − | 0.183 | PD |
| 511 | 46, XX | − | − | − | 0.189 | NA |
| 1 | 46, XY | − | − | − | 0.223 | NA |
| 513 | 46, XX | + | + | − | 0.261 | CR |
| 3 | 47, XX, +8[19]/46, XX[1] | − | − | − | 0.284 | NA |
| 584 | 46, XY | − | − | − | 0.309 | CR |
| 550 | 46, XX | − | − | − | 0.380 | PD |
| 243 | 47, XX, +6[19]/46, XX[2] | − | − | − | 0.443 | CR |
| 214 | 46, XY, t(13; 18)(ql?4; p11.2)[cp3] 46, XY[17] | + | − | − | 0.448 | NA |
| 175 | 47, XX, +13[18]/46, XX[2] | + | − | − | 0.493 | CR |
| 8 | 46, XY | + | − | + | 0.502 | CR |
| 203 | 46, XY | − | − | − | 0.508 | CR |
| 180 | 46, XX, t(16; 16)(p13; q22)[20] | − | − | − | 0.553 | CR |
| 242 | 46, XY, del(20)(q11.2q 13.?1)[20] | − | − | − | 0.586 | CR |
| 210 | 46, XX | + | + | + | 0.611 | CR |
| 201 | 46, XY | + | + | − | 0.618 | PD |
| 13 | 46, XY, t(5; 7)(q31; p22)[cp15]/ 46, XY[6] | − | − | − | 0.645 | PD |
| 632 | 46, XY | − | − | − | 0.661 | NA |
| 17 | 46, XX | + | + | + | 0.664 | CR |
| 227 | 47, XY, t(10; 11)(11qter->11q23.3::11q13.1->11q23.2::10p13->10qter; 11pter->11p13.1::10p13>10pter), add(21)(q22), +dup(21)(q22)[17]/ 48~49, XY, t(10; 11), +21, +21[cp2] | − | − | − | 0.738 | CR |

TABLE 2-continued

CPX-351 Cytotoxicity, Karyotype, and Molecular Lesions of AML Patients.

| Patient ID | Cytogenetics | FLT3-ITD | NPM1 | CEBPα | CPX-351 IC$_{50}$ (uM) | Response to "7 + 3" |
|---|---|---|---|---|---|---|
| 159 | 46, XY, del(11)(q14q23)[14]/ 46, XY[6] | − | − | − | 0.860 | CR |
| 225 | 46, XY | − | + | − | 0.878 | NA |
| 55 | 46, XX, inv(16)(p13q22) | − | − | − | 0.879 | CR |
| 232 | 44, XY, del(7)(q?21q?32), dic(7; 16)(p13; q12-13), −12[cp19]/46, XY[3] | − | − | − | 1.880 | PD |
| 195 | 46, XY | − | + | − | | |
| 113 | 46, XX, t(H; 19)(q23; p13.1)[12]/ 46, XX[8] | − | − | − | 2.828 | CR |
| 197 | 47, XY, +11[19]/46, XY[1] | − | − | − | 5.443 | CR |
| 28 | 46, XY, t(8; 21)(q22; q22)[15]/ 46, XY[5] | − | − | − | 5.938 | NA |
| 206 | 46, XY | − | + | − | 9.770 | NA |

Figure 2A:
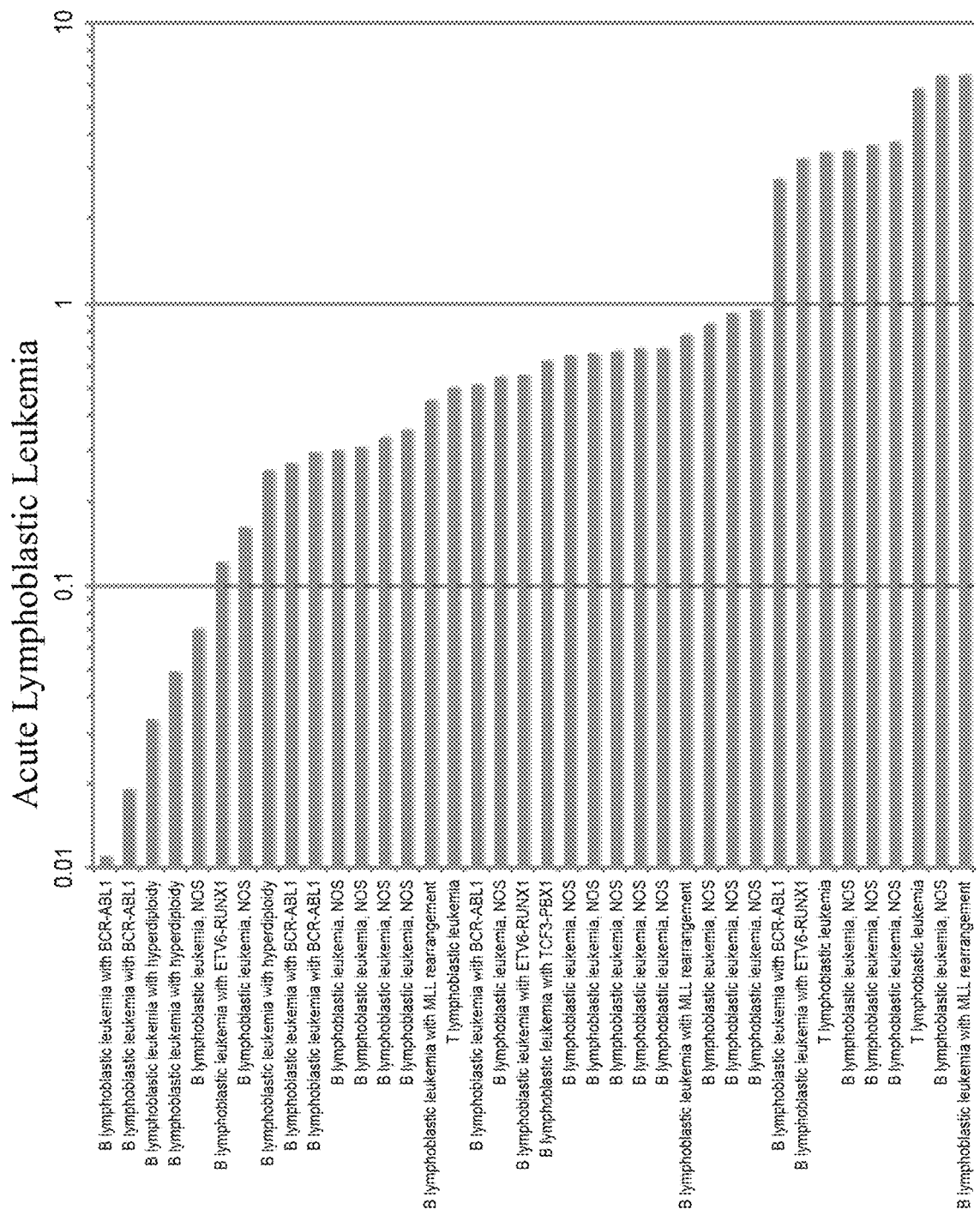
FIGS. 2A-2C, respectively, show the ex vivo sensitivities of ALL, MDS/MPN, and CLL patient cells to CPX-351. Leukemic cells from peripheral blood or bone marrow specimens from 127 patients with ALL, MDS/MPN, or CLL were analyzed. The $IC_{50}$ values for these cases are displayed with specific diagnoses annotated.
Figure 2B:
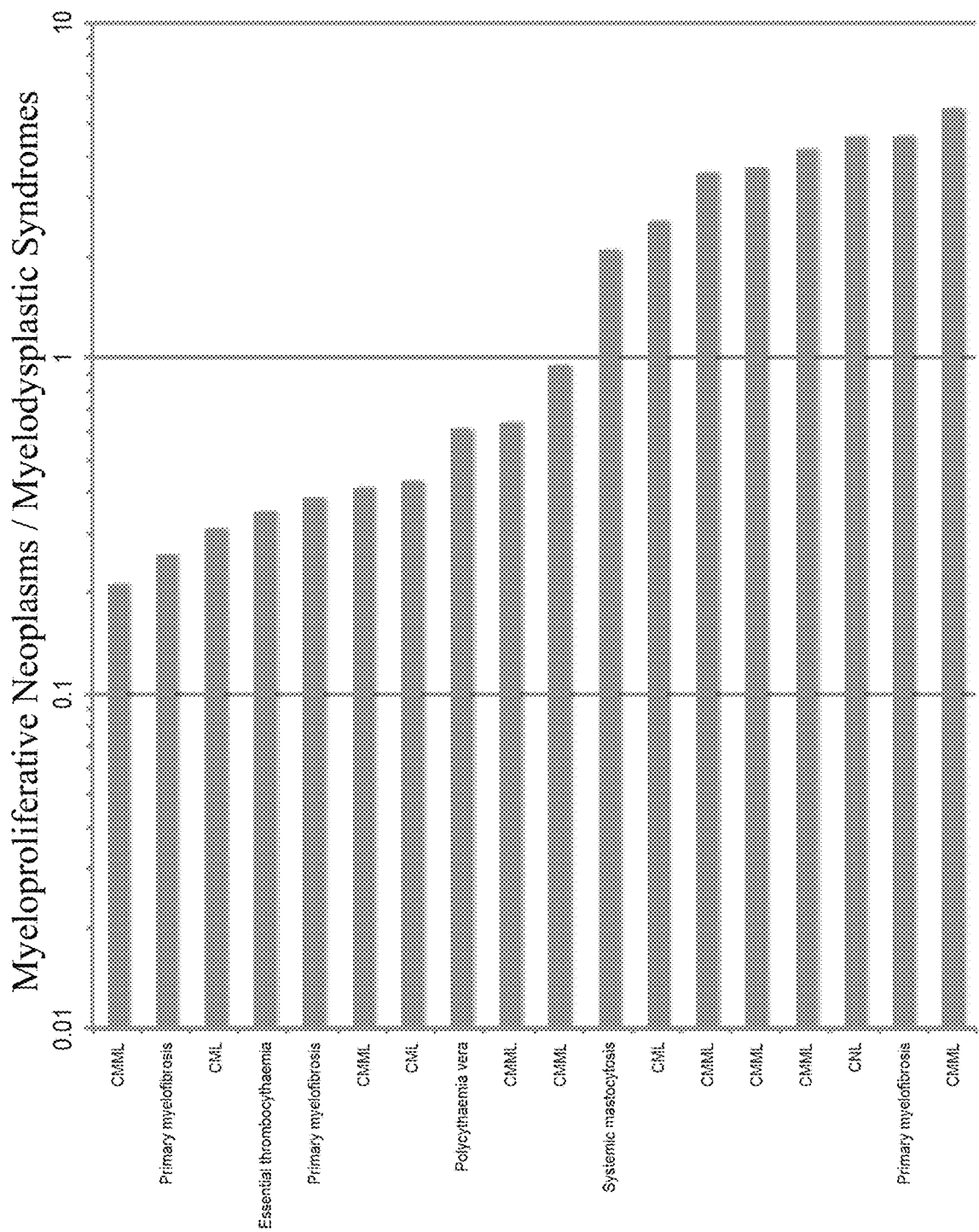
Figure 2C:
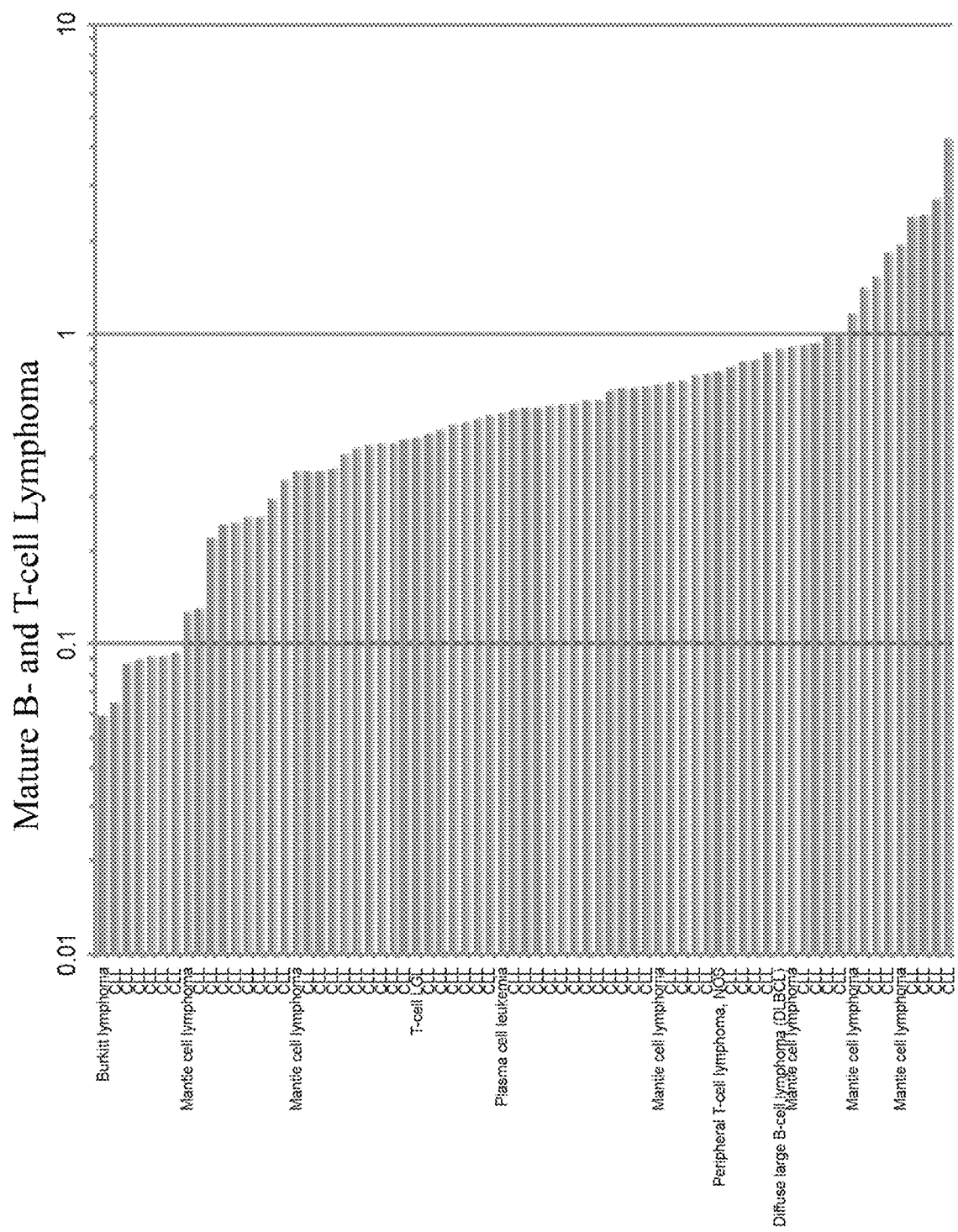

CPX-351 ex vivo sensitivity was also characterized across different subtypes of hematologic malignancy. One hundred and twenty-seven (127) additional patient specimens were employed comprising ALL (38), MPN/MDS (18), and lymphoma (71). The cytotoxic potencies of CPX-351, estimated by the IC$_{50}$, were determined for each individual patient sample ex vivo and are presented in FIGS. 2A-2C. A wide range of IC$_{50}$ values was observed within each diagnostic category (0.03/0.006 μM-10/2 μM). The median IC$_{50}$ for all 180 patient samples testing (including the 53 AML cases) was 0.558:0.112 uM, and the vast majority (153/180, 85%) exhibited IC$_{50}$ values below 2.0:0.4 uM, which is 30-fold lower than the reported 72 hr plasma drug concentrations of 60:12 uM observed in leukemia patients (Gordon, M., et al., *Proceedings of the AACR* (April 2016) 57: Abstract #287). The observed low median IC$_{50}$ of CPX-351 relative to circulating drug concentrations indicated a generally high potency of CPX-351 in potentially inhibiting proliferation or survival of leukemic cells from a broad range of diagnoses.

Example 2

Effect of Gene Mutations

Figures 3A, 3B, 3C:
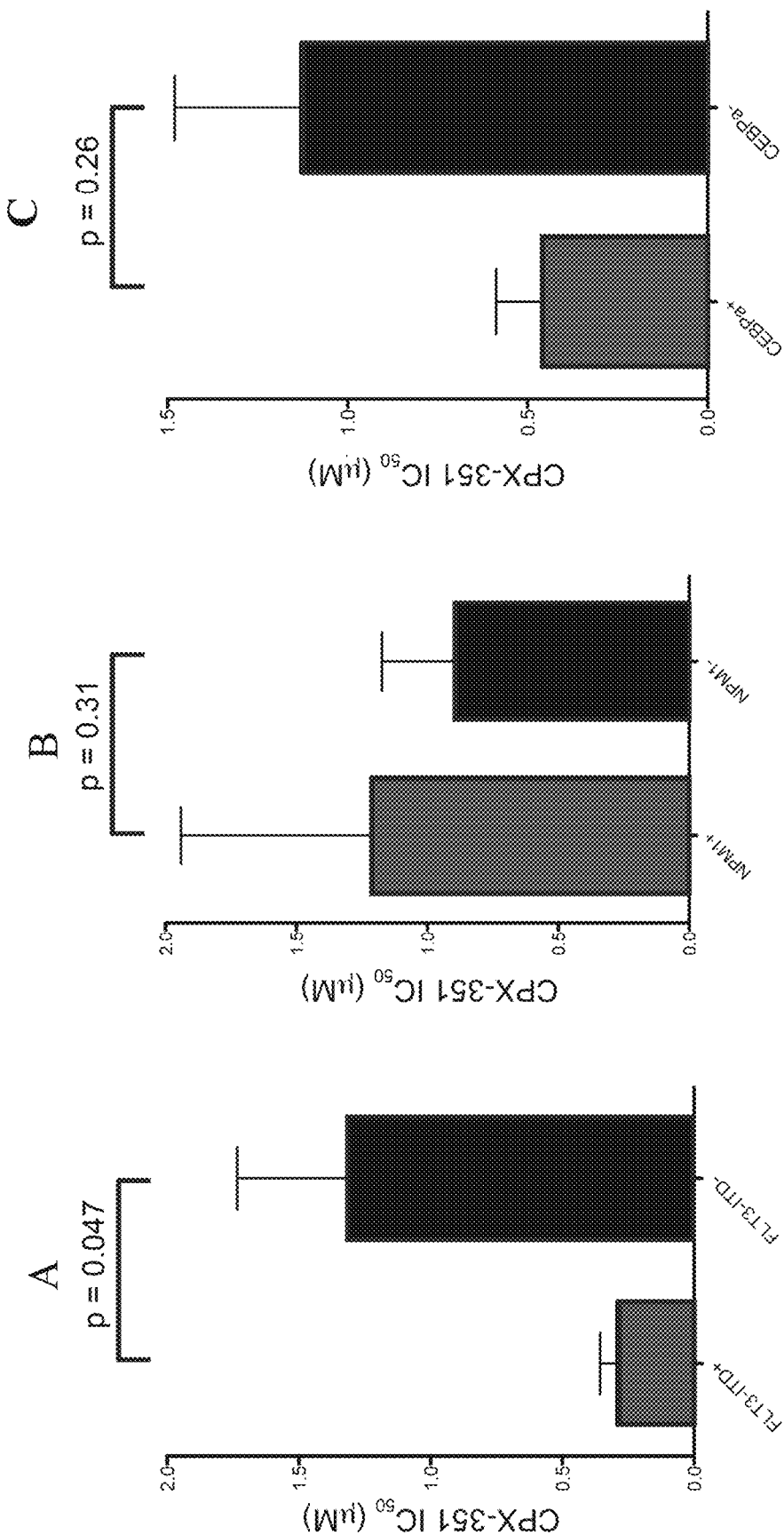
FIG. 3A is a graph showing that AML cells with FLT3-ITD exhibit increased sensitivity to CPX-351-induced cytotoxicity. FLT3-ITD was positive in 14 patients, negative in 28.
FIGS. 3B and 3C, respectively, show results for subjects with mutated NPM-1 and CEBPα. Insertions in NPM-1 were identified in 13 patients and not observed in 29; Insertion/deletion of CEBPα was observed in 4 patients and not detected in 34. Values represent mean±s.e.m. with p-values displayed on each chart.

Greater CPX-351 potency is observed in AML patient blasts with the FLT3-ITD phenotype: FMS-like tyrosine receptor kinase (FLT3) plays an important role in normal hematopoiesis and leukemogenesis and is expressed in most AML blasts. In 20% to 25% of AML patients, the FLT3 gene acquires an internal tandem duplication in the juxtamembrane domain of FLT3 (FLT3-ITD), and is associated with poor patient prognosis. Among 42 AML patients in the study of Example 1 with known FLT3-ITD status, 14 patients were identified as the carriers for FLT3-ITD mutation and the remaining 28 were FLT3-ITD negative. The ex vivo cytotoxicity results indicated that FLT3-ITD positivity was surprisingly associated with a higher sensitivity to CPX-351-induced cytotoxicity (as shown in FIG. 3A). Specifically, leukemia blasts displaying FLT3-ITD showed substantially lower IC$_{50}$ values (0.29:0.058 μmol) compared to FLT3-ITD negative patient blast samples (IC$_{50}$=1.32:0.26 μmol). This difference in response to CPX-351 cytotoxicity between FLT3-ITD positive and negative samples was statistically significant (p=0.047). It was also noted that FLT3-ITD positive patients had a significantly higher white blood cell count (WBC) with a mean of 91,000/mm$^3$ versus 29,000/mm$^3$ at diagnosis, p=0.0002.

Other common mutations including nucleophosmin (NPM1) and CCAAT/enhancer binding protein alpha (CEBPα) were also found in 13 and 4 patients, respectively. However neither of these two common mutations showed a significant impact in CPX-351 treatment response ex vivo though there was a trend towards greater sensitivity in cases positive for CEBPα. (FIGS. 3B and 3C.)

Example 3

Correlation Between Ex Vivo Sensitivity and CPX-351 Uptake in Patient Leukemia Blasts Preclinical leukemia animal models demonstrated that upon CPX-351 injection, leukemic cells in engrafted bone marrow in these animals could quickly take up cytarabine and daunorubicin, largely in the intact liposomal form with the synergistic drug ratio maintained, resulting in increased and prolonged drug accumulation in leukemic cells as compared to free-drug cocktail administration. The data below show enhanced uptake of CPX-351 as compared to free drug. Thus, uptake and cytotoxicity ex vivo of CPX-351 can be employed to predict clinical CPX-351 success.

Viably frozen cells from patient specimens previously screened for ex vivo CPX-351 sensitivity were exposed to the maximally tested concentration of CPX-351 (10:2 μM cytarabine:daunorubicin) for 24 hours. Cells were then washed 3 times with PBS and analyzed for uptake of daunorubicin fluorescence using a BD FACSAria flow cytometer.

Figure 4A:
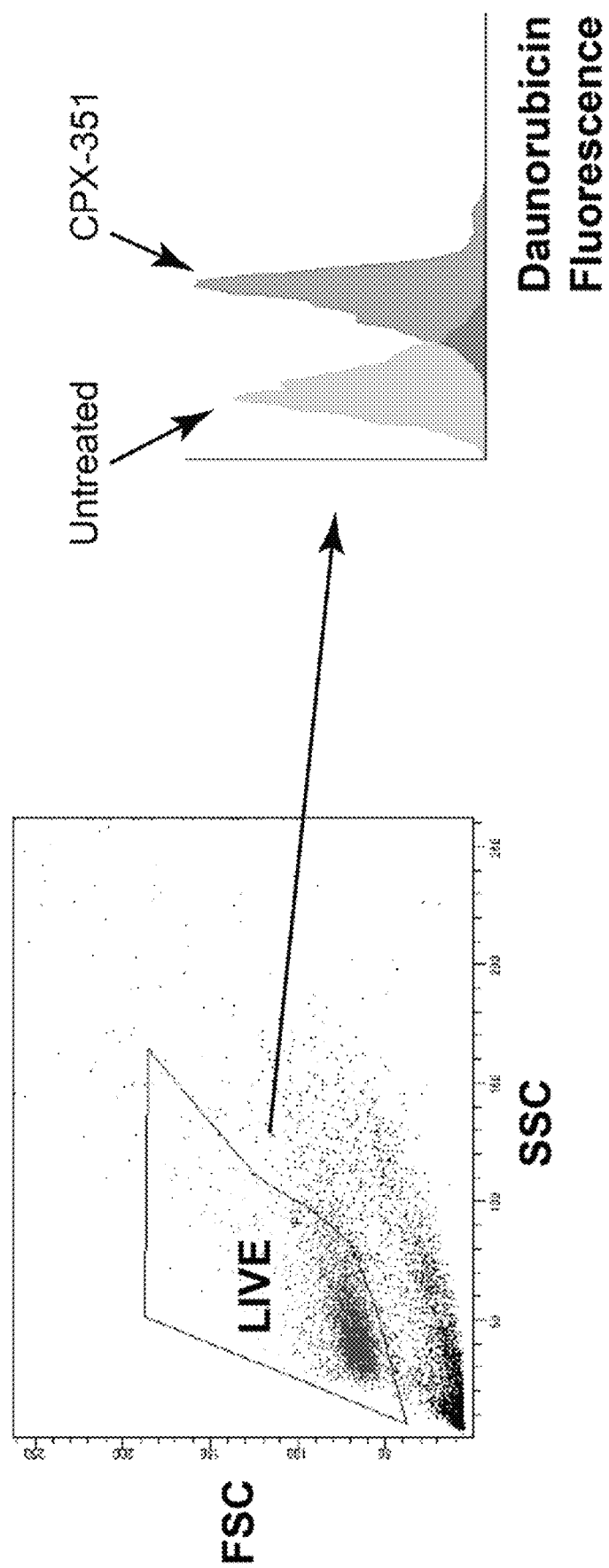
FIGS. 4A-4C show the flow cytometric analysis of CPX-351 drug uptake and results demonstrating correlation between drug uptake and cytotoxicity are obtained.

Flow cytometric analysis was performed on 12 patient samples as described above utilizing the inherent fluorescence of daunorubicin as a semi-quantitative indicator of intracellularly bioavailable drug. The samples were of 6 AML and 6 CLL and exhibited a broad range of IC$_{50}$ values on initial ex vivo screening. Cells were exposed to graded concentrations of CPX-351 for 24 hours before being analyzed for the uptake of daunorubicin on a BD FACSAria flow cytometer. Live cells were identified in the scatter plot of FSC vs. SSC and total fluorescence intensity was quantified (FIG. 4A, left). The ratio of mean fluorescent intensity of cells exposed to CPX-351 relative to untreated cells was used to generate an index of drug uptake with an index of 1 indicating no uptake and numbers greater than 1 indicating uptake of daunorubicin.

Statistical Analysis: an unpaired t-test with one-tailed p-value was used to compare CPX-351 activity in mutated versus wild-type FLT3 (ITD), NPM1 and CEBPα groups. A p-value of <0.05 was considered significant. A one-way ANOVA analysis was used to compare outcomes between multiple genetic-cytogenetic risk groups. Statistical analysis was performed using Prism software version 5.0a.

Figure 4B:
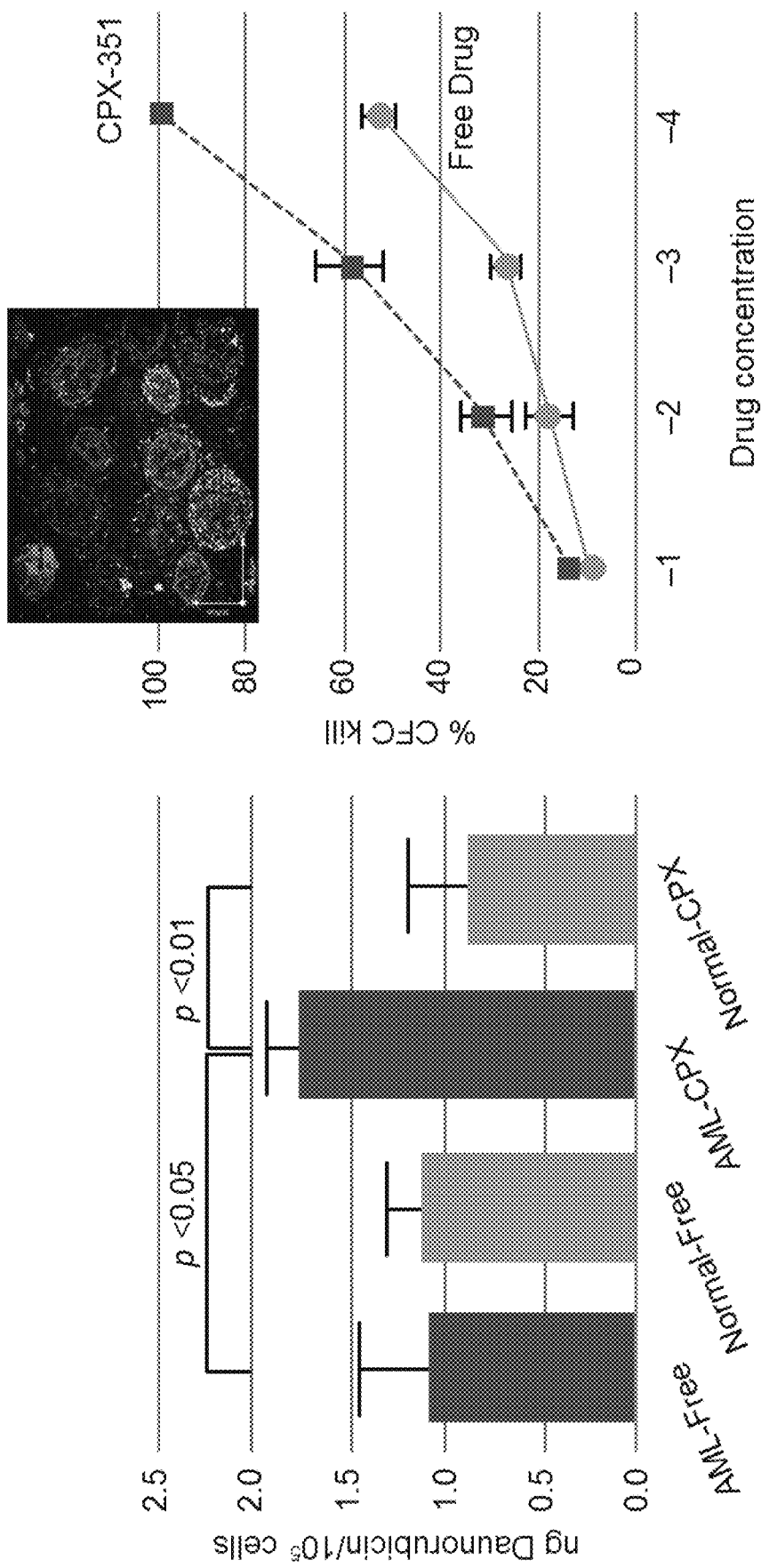
Figure 4C:
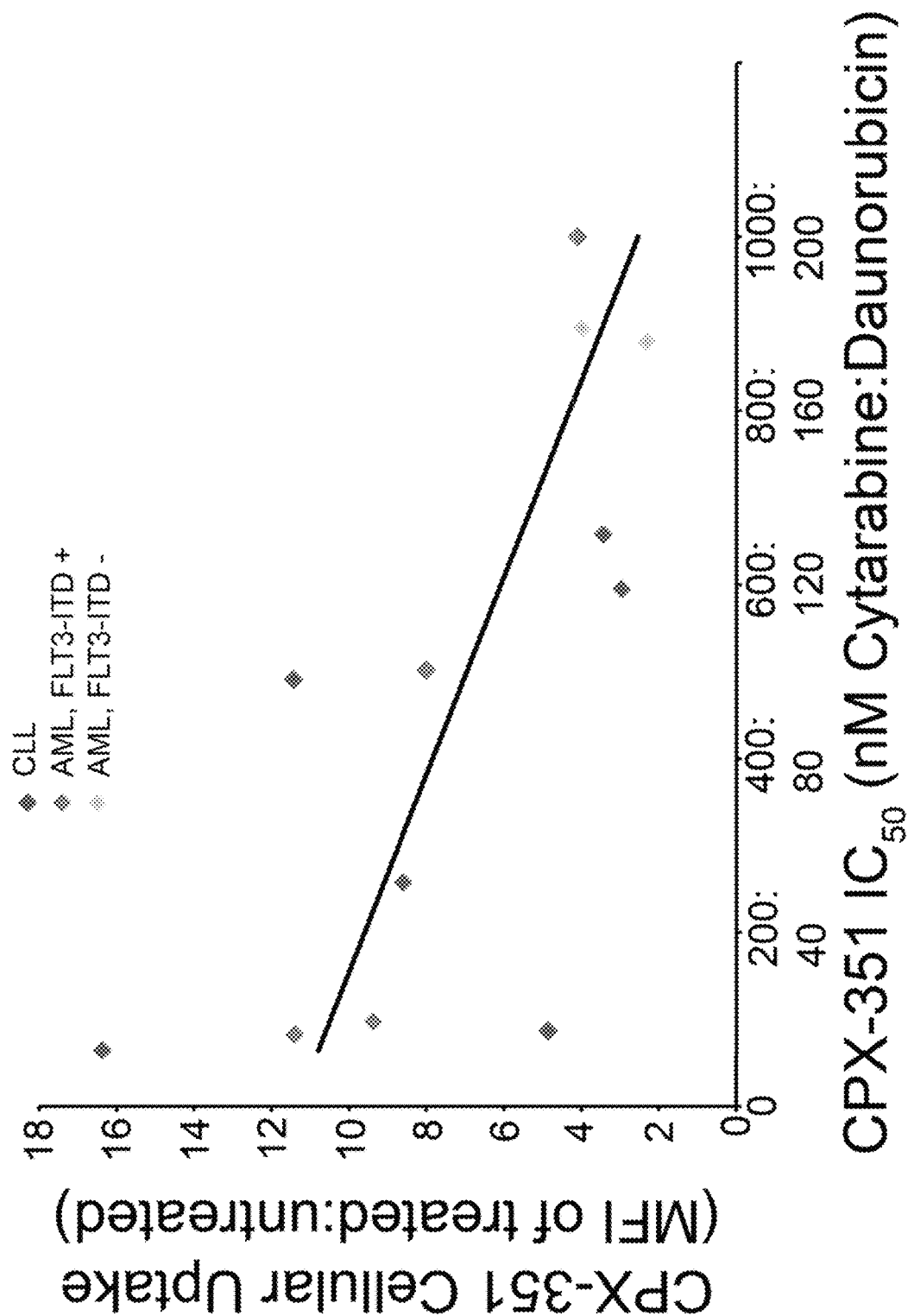

Compared to untreated cells, cells treated with CPX-351 showed a marked increase in the amount of intracellular fluorescence intensity, indicating the presence of free daunorubicin as the fluorescence of daunorubicin encapsulated inside CPX-351 is completely quenched. Differences between treated and untreated cell samples in daunorubicin uptake are shown as the fold shift in mean fluorescent intensity (MFI) (FIG. 4A, right). FIG. 4B shows the comparison of uptake and cytotoxicity. When the values of CPX-351 $IC_{50}$ on these 12 samples were plotted against the corresponding values of MFI, a strong correlation between cell sensitivity to CPX-351 ($IC_{50}$) and efficiency in CPX-351 uptake (MFI) was revealed with a correlation coefficient of 0.703 (FIG. 4C).

Figures 5A, 5B, 5C:
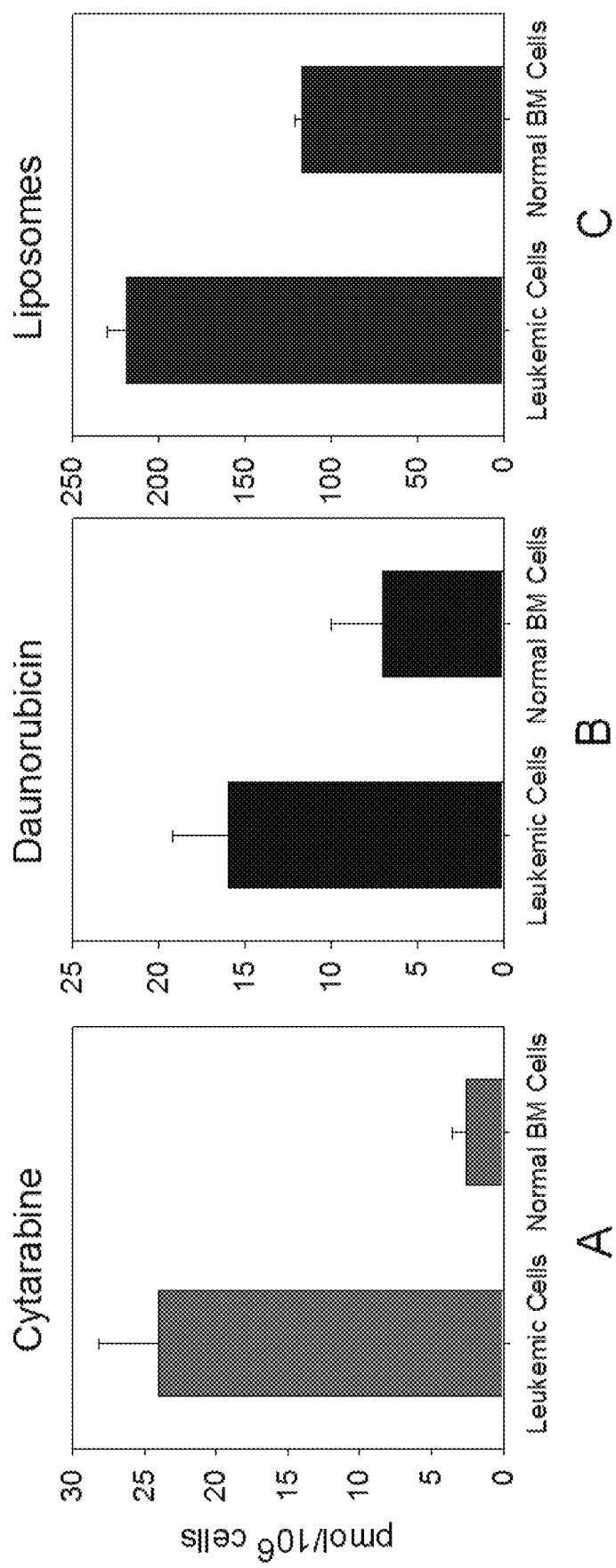
FIGS. 5A-5C show the uptake of intact CPX-351 by leukemic cells in the bone marrow in comparison to normal bone marrow cells.

Selective uptake by leukemia bone marrow cells leaving CPX-351 intact was shown as follows: Femoral bone marrow cells of CCRF-CEM (leukemia) engrafted mice treated with 1 dose of CPX-351 were collected at 18 hours after drug administration. Leukemic and normal bone marrow cells were separated by human CD45-specific magnetic beads and analyzed for CPX-351 uptake. Cytarabine and liposomal lipids were $^3$H and $^{14}$C-labeled, respectively, and quantitated by liquid scintillation. Daunorubicin was analyzed by HPLC. The results are shown in FIGS. 5A-5C. Each bar represents the mean±SE of 3 replicates with 10 femurs (5 mice) per replicate.

As shown in FIG. 5C, approximately 225 pmol of liposomal labeled lipid per $10^6$ cells was taken up by leukemic cells, but an uptake of only approximately 110 pmol/$10^6$ cells by normal bone marrow. The level of the drugs contained in the liposomes also was preferably taken up by leukemic cells wherein cytarabine showed an uptake of 24 pmol/$10^6$ cells and daunorubicin about 16 pmol/$10^6$ cells for leukemic cells and, in each case, but lower levels for normal bone marrow (about 3 pmol/$10^6$ cells for cytarabine and about 7 pmol/$10^6$ cells for daunorubicin). The molar ratio of liposomal lipid to the drug contained therein is approximately 10:1 so that these results demonstrate that the drugs remained in the liposomes when taken up by these cells.

Example 4

CPX-351 Demonstrates Superior Antitumor Efficacy in FLT3-ITD+ AML Patients

In this example, a Phase 3 clinical trial was undertaken wherein AML patients were screened to determine whether they carry an activating mutation in the FLT-3 gene. Those AML patients found to have the activating mutation AML-ITD+ were administered 3 doses of CPX-351 in a cycle of administration consisting of a first administration step on day 1, a second administration step on day 3, and a third administration step on day 5. Treatment protocols using CPX-351 is described in U.S. Pat. No. 8,092,828. Patient response, including plasma and/or bone marrow sample analysis, were measured and monitored, and response rates and survival measured. Subsets of patients who were positive for a mutation in NPM1 and/or CEBPα were also included. The initial study focused on FLT-3 mutations, individuals with mutations in NPM-1 and CEBPα were also included. The patients participating in the study are shown in Table 3.

TABLE 3

| Study 301 Mutated Patient Baseline Characteristics | | CPX-351 n = 47 | n (%) | 7 + 3 n = 37 | n (%) |
|---|---|---|---|---|---|
| Age | 60-69 | 31 | (66.0) | 21 | (56.8) |
|  | 70-75 | 16 | (34.0) | 16 | (43.2) |
| PS | 0-1 | 39 | (83.0) | 29 | (78.4) |
|  | 2 | 8 | (17.0) | 9 | (24.3) |
| Karyotype | Non-poor | 28 | (59.6) | 21 | (56.8) |
|  | Adverse | 16 | (34.0) | 11 | (29.7) |
|  | Unknown | 3 | (6.4) | 5 | (13.5) |
| Strata | tAML | 9 | (19.1) | 6 | (16.2) |
|  | MDS with prior HMA* | 15 | (31.9) | 17 | (45.9) |
|  | MDS without prior HMA | 9 | (19.1) | 2 | (5.4) |
|  | CMML | 6 | (12.8) | 5 | (13.5) |
|  | de novo | 8 | (17.0) | 7 | (18.9) |
| Mutation | FLT-3-ITD | 22 | (46.8) | 16 | (43.2) |
|  | FLT-3-TKD | 6 | (12.8) | 9 | (24.3) |
|  | NPM-1 | 15 | (31.9) | 12 | (32.4) |
|  | CEBPα | 14 | (29.8) | 5 | (13.5) |

*hypomethylating agent

The responses with respect to subjects with and without FLT-3 mutations are shown in Table 4.

TABLE 4

| Response (responders/number of patients) | | |
|---|---|---|
|  | CPX-351 | 7 + 3 |
| FLT-3 mutated | 15/22 | 5/20 |
| FLT-3-ITD | 12/19 | 3/13 |
| FLT-3-TKD | 3/3 | 2/7 |

Figure 6:
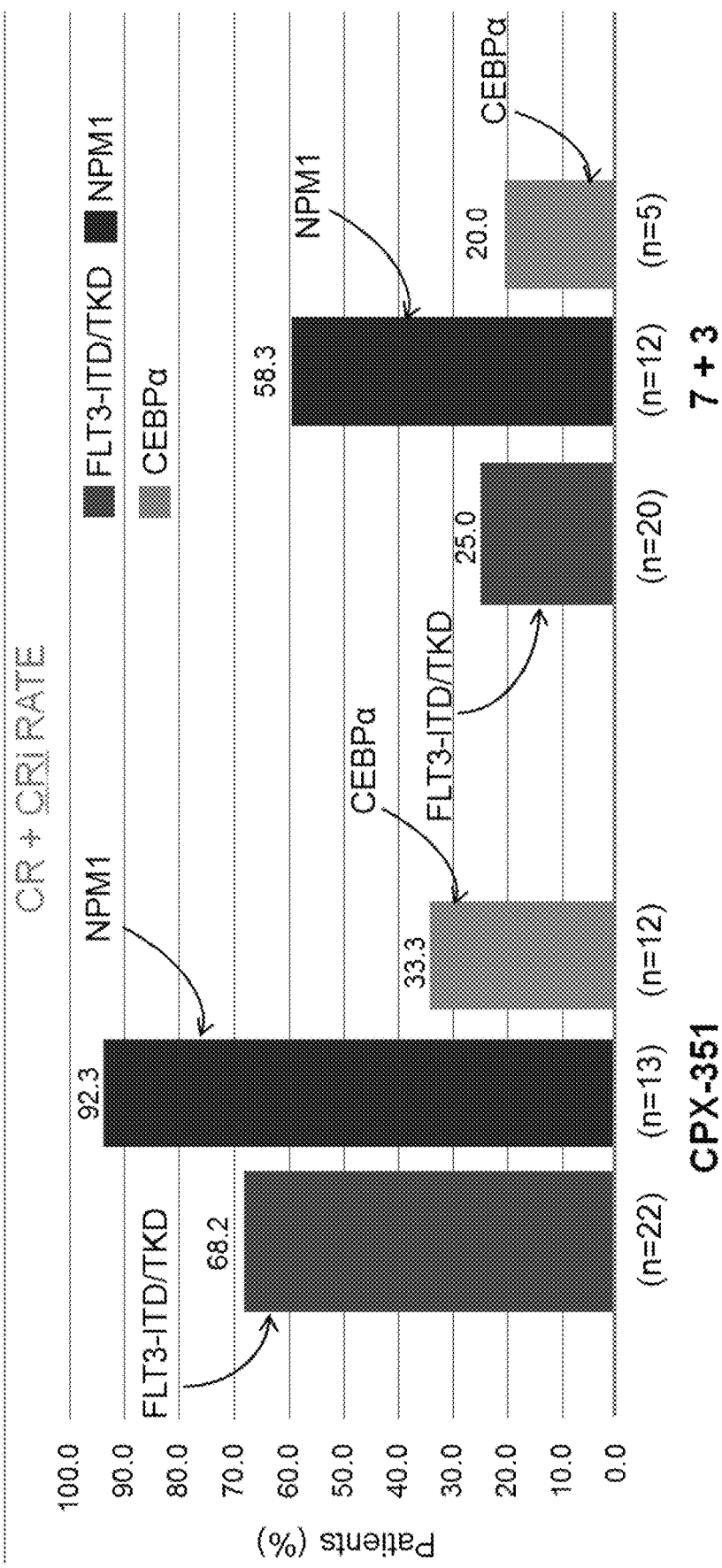
FIG. 6 shows the response rates of FLT-3, NPM-1 and CEBPα mutated patients treated with CPX-351 in clinical trials when compared to standard 7+3 treatment.

FIG. 6 shows the response rates as a comparison between CPX-351 and 7+3 treatment for carriers of these mutations. As shown in FIG. 6, carriers of either ITD or TKD mutation in FLT-3 showed a 68.2% response rate to CPX-351 but only a 25.0% response rate to 7+3. Patients with an NPM-1 mutation showed a 92.3% response rate for CPX-351 but only a 58.3% response rate for 7+3. For individuals with CEBPα mutations, the response rate for CPX-351 was 33.3% and that for 7+3 was 20.0%.

The survival rates for both FLT-3 mutation positive and FLT-3 mutation negative participants in this study are shown in Table 5.

TABLE 5

| | Survival | | | | | |
|---|---|---|---|---|---|---|
| | CPX-351 (n) | | 7 + 3 (n) | | | |
| | n (%) | Median Survival (95% Conf. Int.) | n (%) | Median Survival (95% Conf. Int.) | Hazard Ratio (95% Conf. Int.) | p-value (1-sided) |
| FLT-3 Mutation Positive | 22 (14.4) | 10.25 (5.62, 14.95) | 20 (12.8) | 4.55 (1.45, 10.32) | 0.57 (0.24, 1.33) | 0.093 |
| FLT-3 Mutation Negative | 115 (75.2) | 9.33 (5.68, 12.58) | 115 (73.7) | 5.95 (4.27, 7.82) | 0.65 (0.47, 0.89) | 0.004 |

Figure 7A:
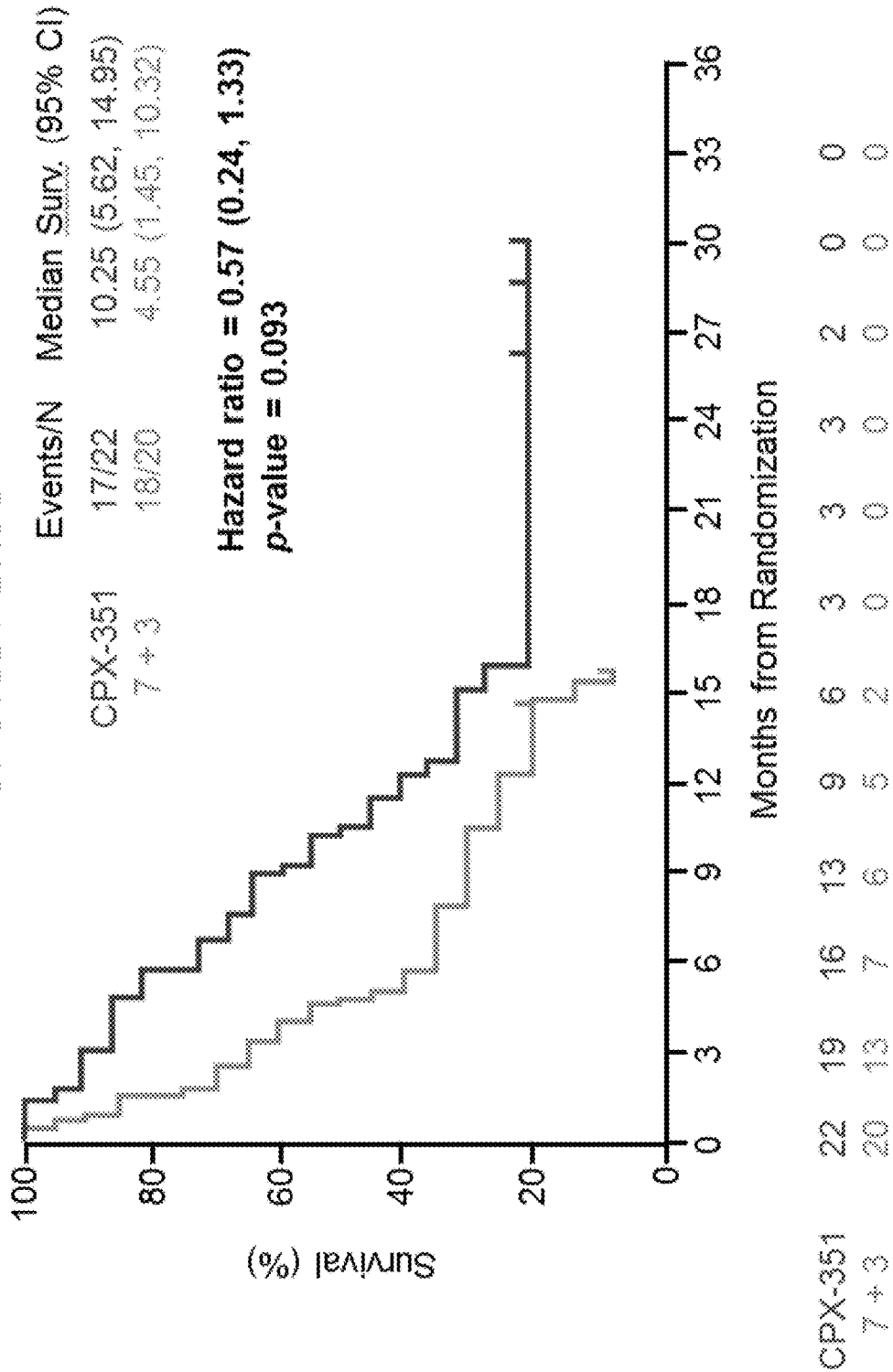
FIGS. 7A-7C show comparison of survival rates of CPX-351 treated patients as compared to standard 7+3 treated patients with FLT-3, NPM-1 and CEBPα mutations, respectively.
Figure 7B:
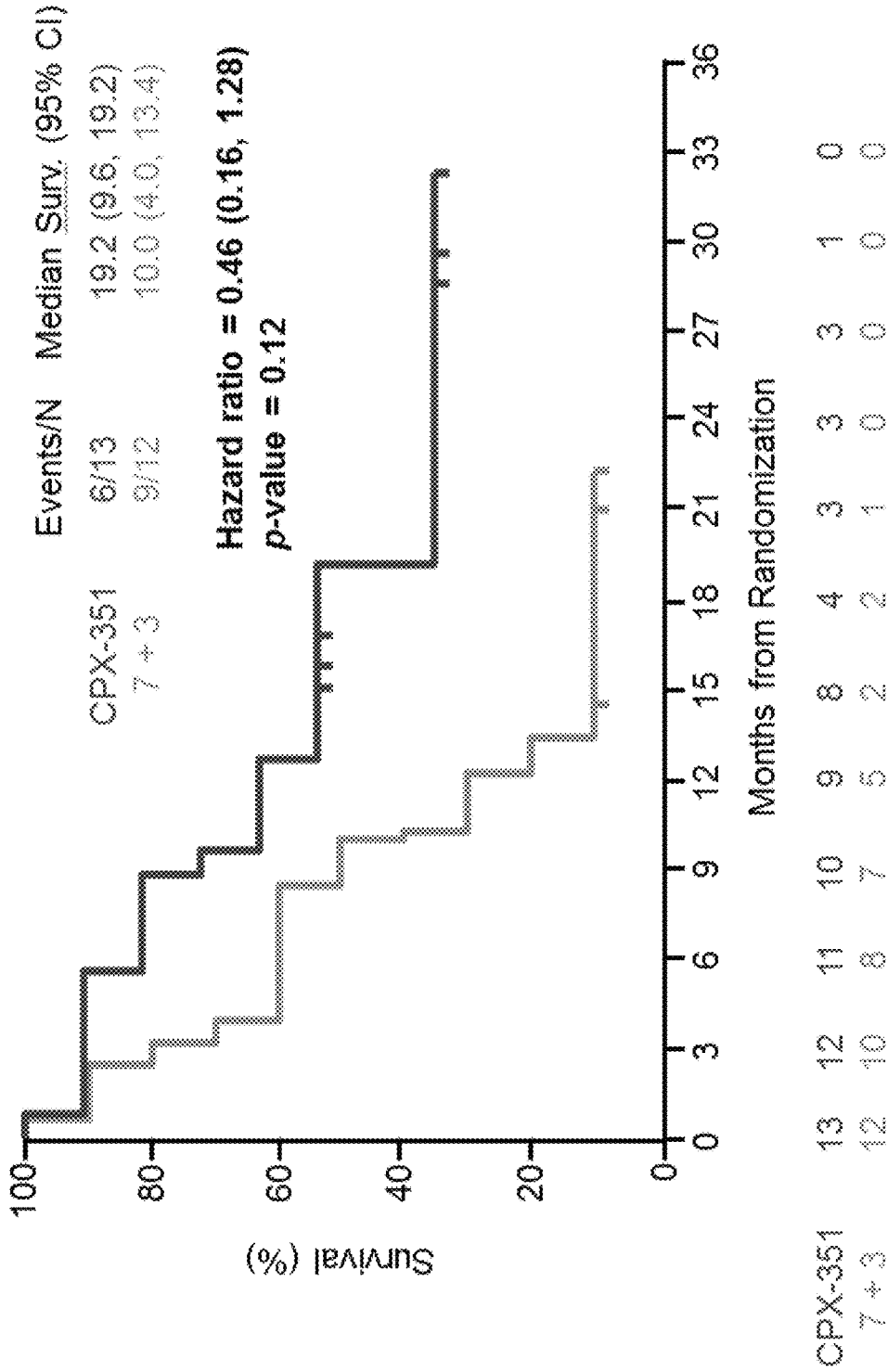
Figure 7C:
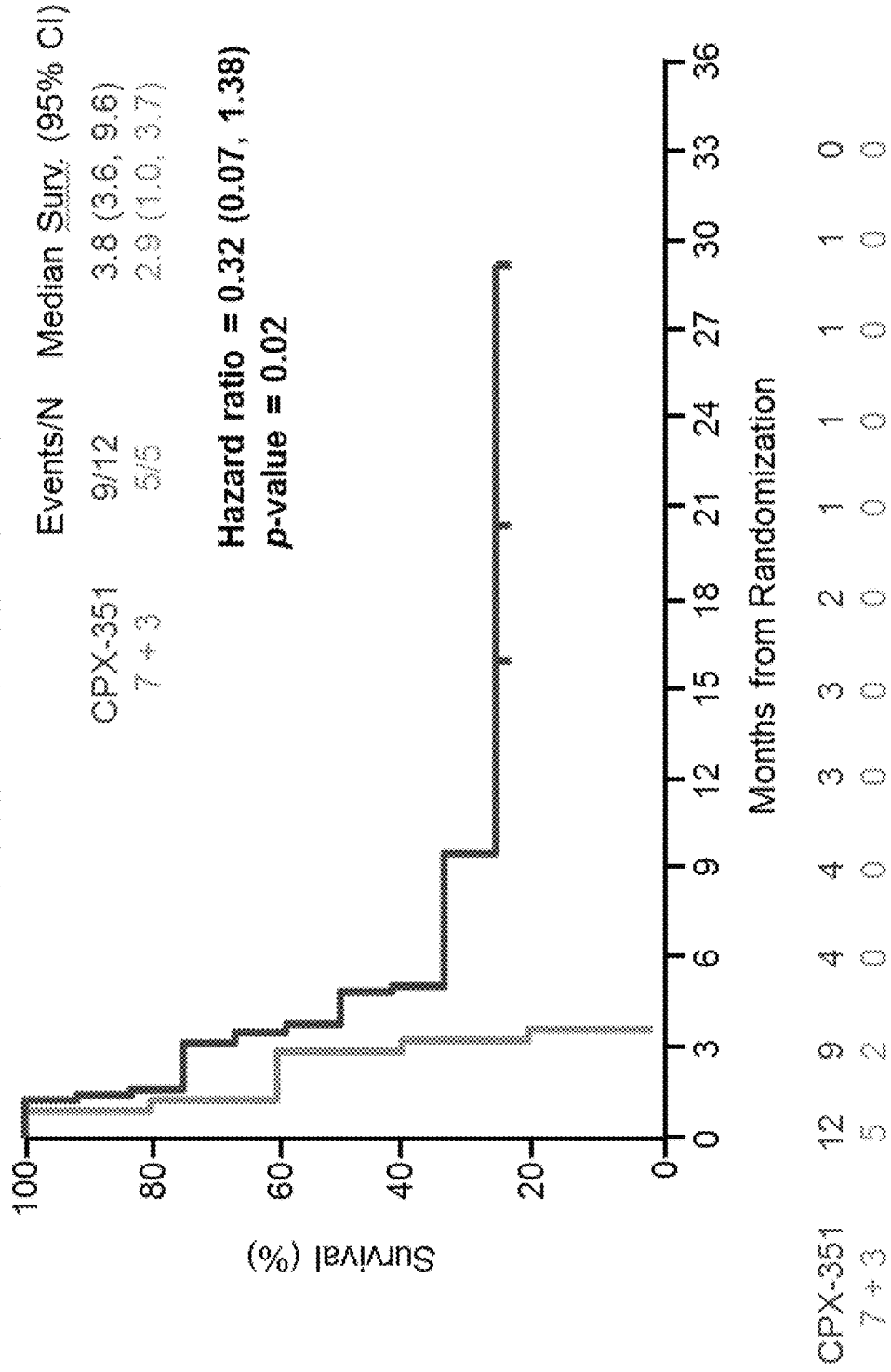

Survival rates for the various cohorts are also shown in FIGS. 7A-7C. In all cases, the survival was greatly improved for carriers of mutations; in particular, 25% of subjects with mutation in CEBPα showed survival of over 27 months when treated with CPX-351 whereas none of the patients treated with 7+3 survived for over three months.

Example 5

Susceptibility of FLT-3 Mutated Cells to CPX-351 and Combination Treatment: CPX-351+FLT-3 Inhibitor In this Example, cell viability and intracellular uptake based on daunorubicin fluorescence determined by flow cytometry, were measured as described in Examples 1 and 3.

Figure 8A:
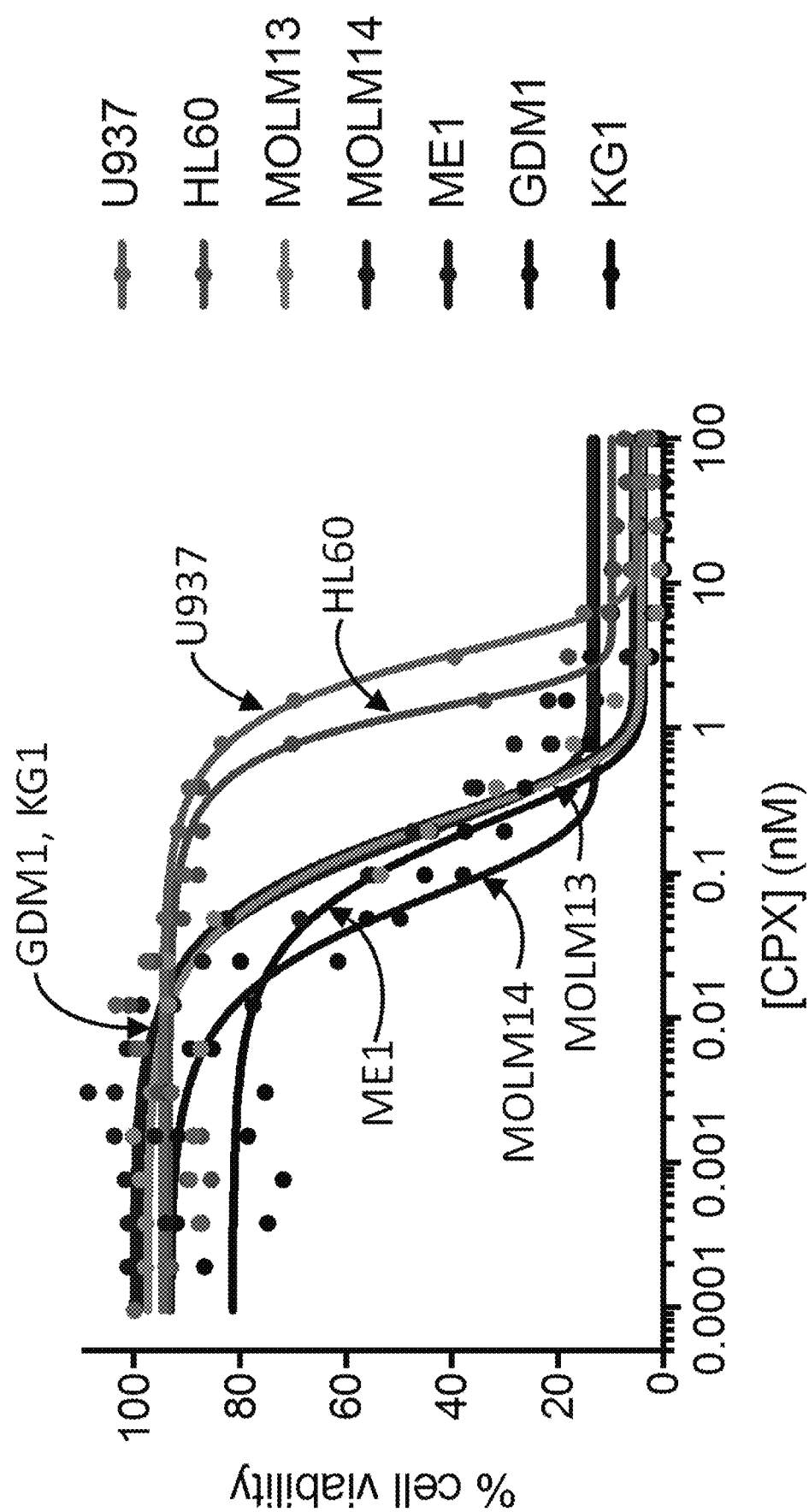
FIGS. 8A and 8B show comparison of $IC_{50}$ values (FIG. 8A) and normalized measures of CPX-351 uptake (FIG. 8B) for various cell lines including those with and without FLT-3 mutations.
Figure 8B:
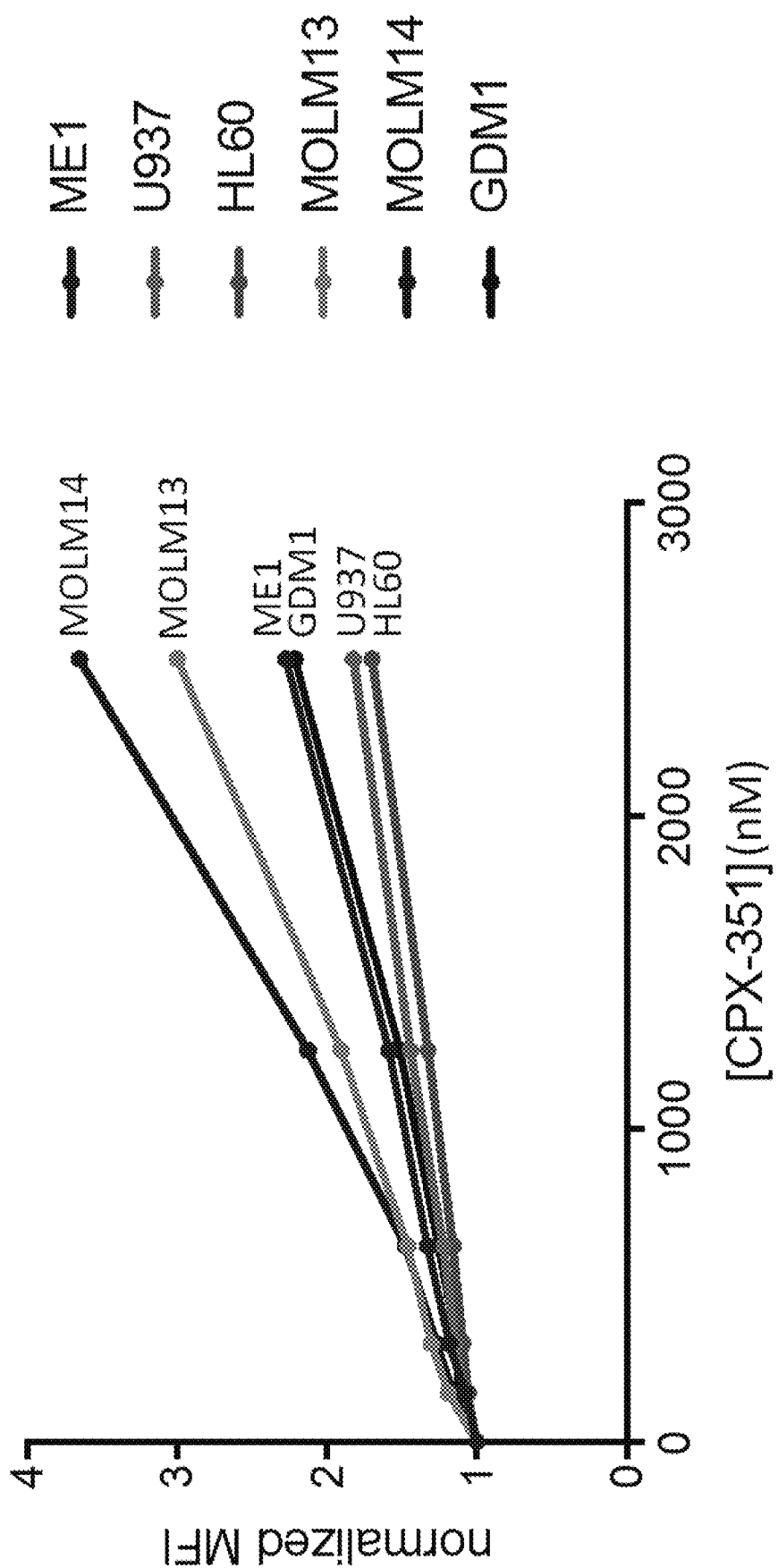

A. Susceptibility of AML cell lines (including MOLM-13 and MOLM-14 that contain FLT-3-ITD and ME-1 (that contains mutant, activated FLT-3) to CPX-351 and uptake of CPX-351 by these cells were determined. Cells that do not contain FLT-3 mutations including U-937, HL-60, KG-1 and GDM-1 were also compared. Cultures of these cells were treated with CPX-351 and assayed for $IC_{50}$ and CPX-351 uptake. FIG. 8A shows the results with respect to $IC_{50}$ by plotting the percent cell viability against nM concentration of CPX-351. As seen in FIG. 8A, the FLT-3 mutated cells have lower $IC_{50}$'s than non-FLT-3 mutated cells. FIG. 8B shows the results of uptake; the concentration of CPX-351 in nM is plotted vs. the mean fluorescence intensity (MFI) normalized to take account of inherent fluorescence. Cells that contain FLT-3 mutations are more effective in taking up CPX-351 than those that do not.

Figures 9A, 9B:
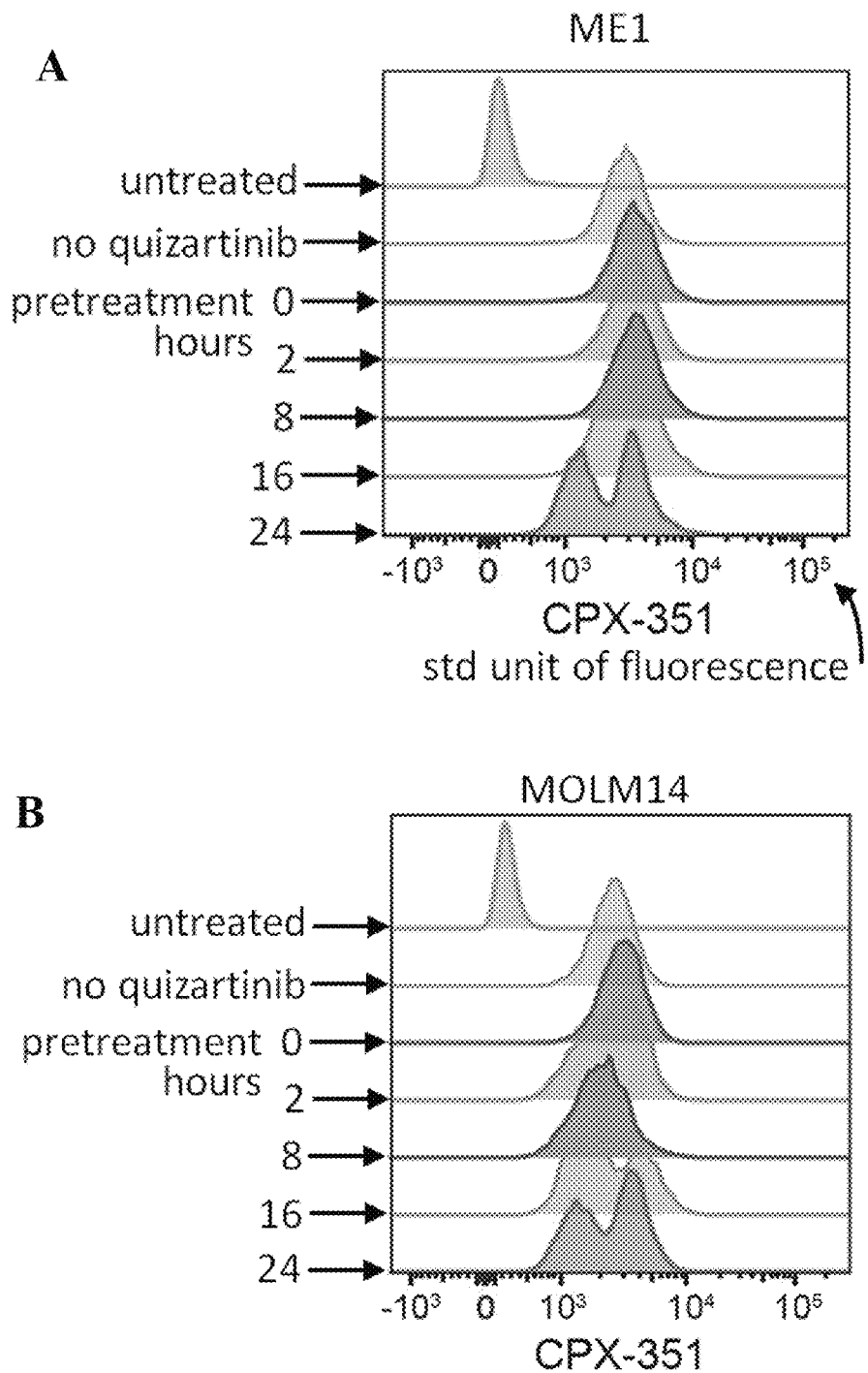
FIGS. 9A-9D show a comparison of CPX-351 uptake in the presence and absence of pretreatment with quizartinib for two different cell lines with FLT-3 mutations.
Figures 9C, 9D:
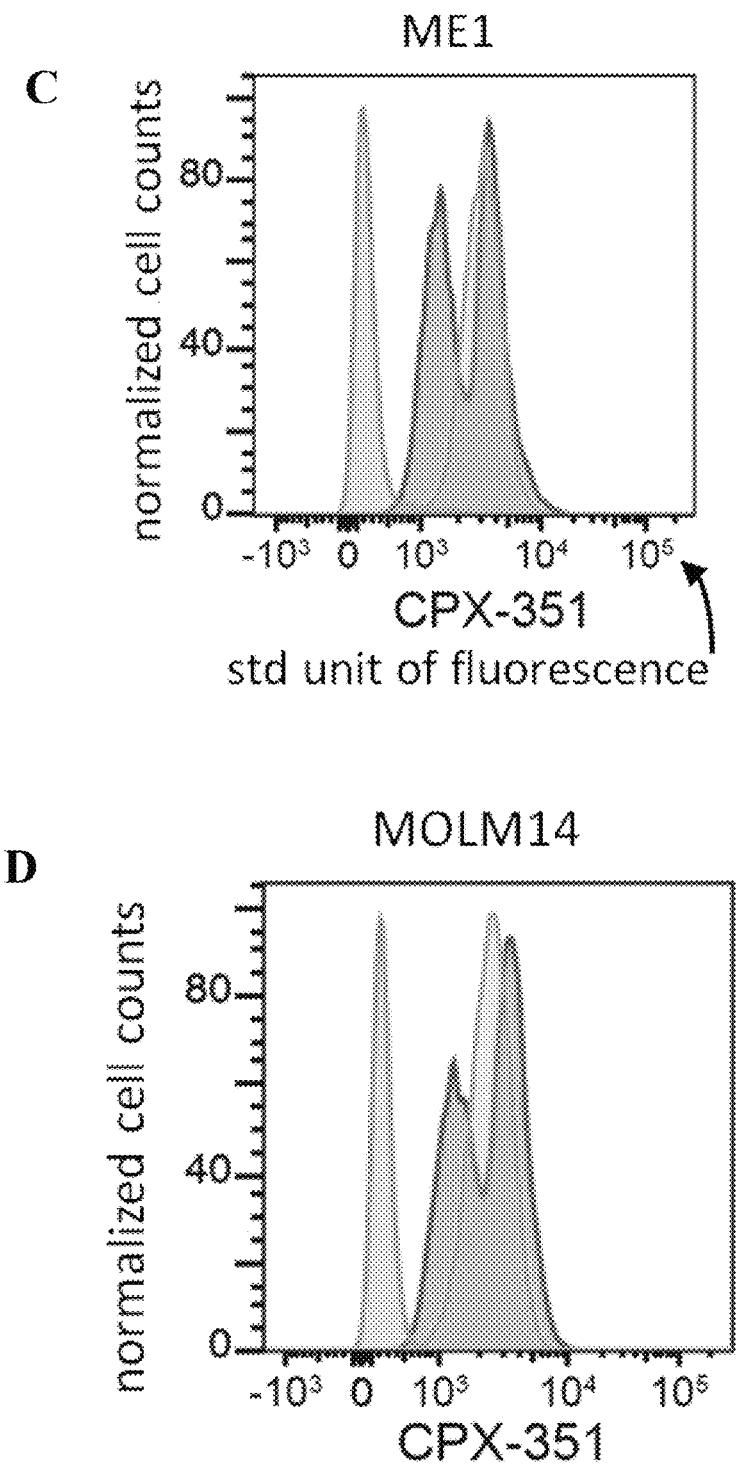

B. To determine the effect of combining treatment with FLT-3 inhibitors, cells were exposed to CPX-351, with or without treatment with quizartinib or midostaurin (FLT-3 inhibitors). In one protocol ME-1 and MOLM-14 cells were exposed to pretreatment with 10 nM quizartinib for 0, 2, 8, 16 and 24 hours after which 100 μM of CPX-351 was added for 2 hours. Uptake of CPX-351 was measured by daunorubicin fluorescence as determined by flow cytometry normalized to untreated control. The results are shown in FIGS. 9A-9D. The x-axis in the graphs depicts the uptake of CPX-351 in standard units of fluorescence and the y-axis represents the normalized cell counts. As shown in FIGS. 9A and 9B, all of the untreated cells showed no uptake whereas cells treated with CPX-351 were ultimately sorted into two cell populations one of which was more effective in CPX-351 uptake than the other. It is clear from FIGS. 9A and 9B that as the pretreatment time is extended, the ability of some of the cells to take up CPX-351 is diminished. The results in FIGS. 9C and 9D are composites of the various timepoints up to 24 hours.

C. To determine synergy, cell lines were plated onto 384-well plates and exposed to customized dose-escalating concentrations of CPX-351 and FLT-3 inhibitor. CPX-351 and FLT-3 inhibitors were either added (a) simultaneously (C+Q or C+M), (b) with 24-hour CPX-351 pretreatment (C→Q or C→M), or (c) 24-hour FLT-3 inhibitor pretreatment (Q→C or M→C). To determine synergy for each drug combination, the EOBA algorithm was employed.

Figure 10A:
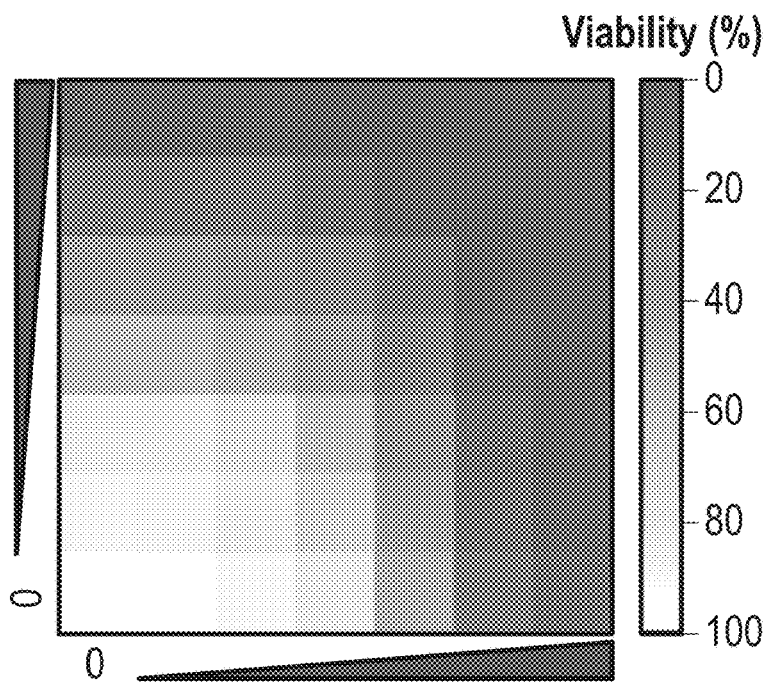
FIGS. 10A-10C show the results of determination of synergistic interaction between CPX-351 and either quizartinib or midostaurin.
Figure 10B:
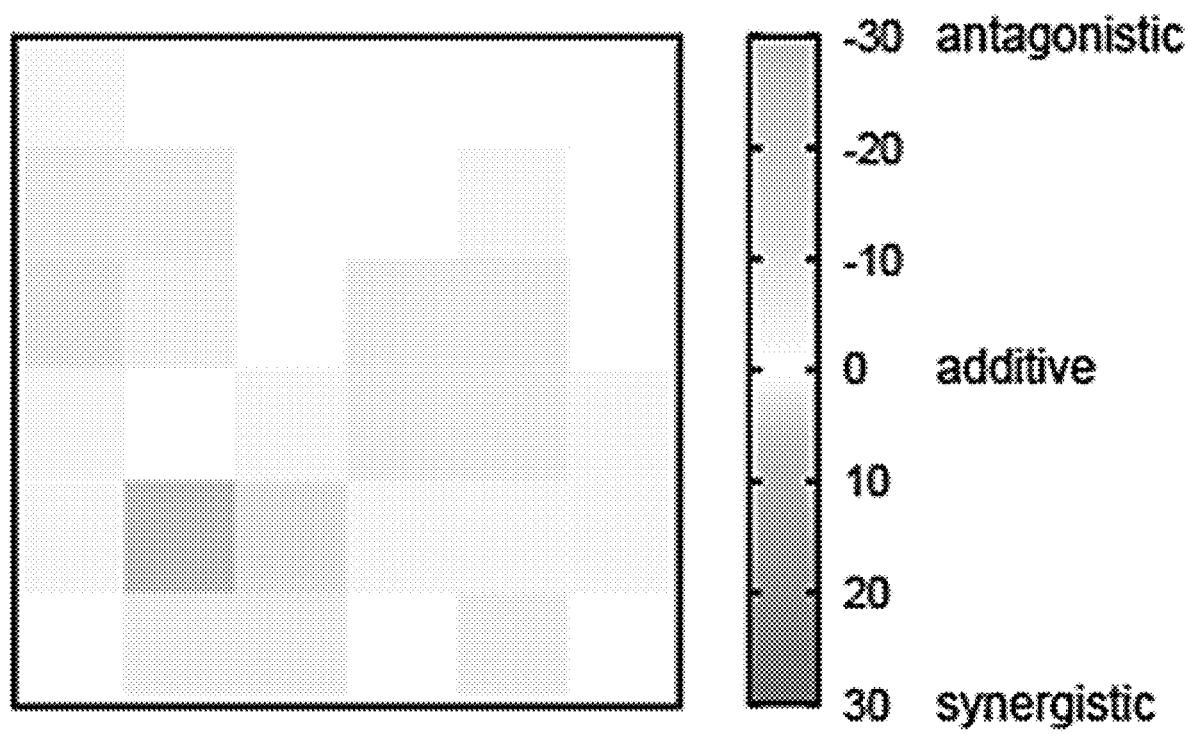
Figure 10C:
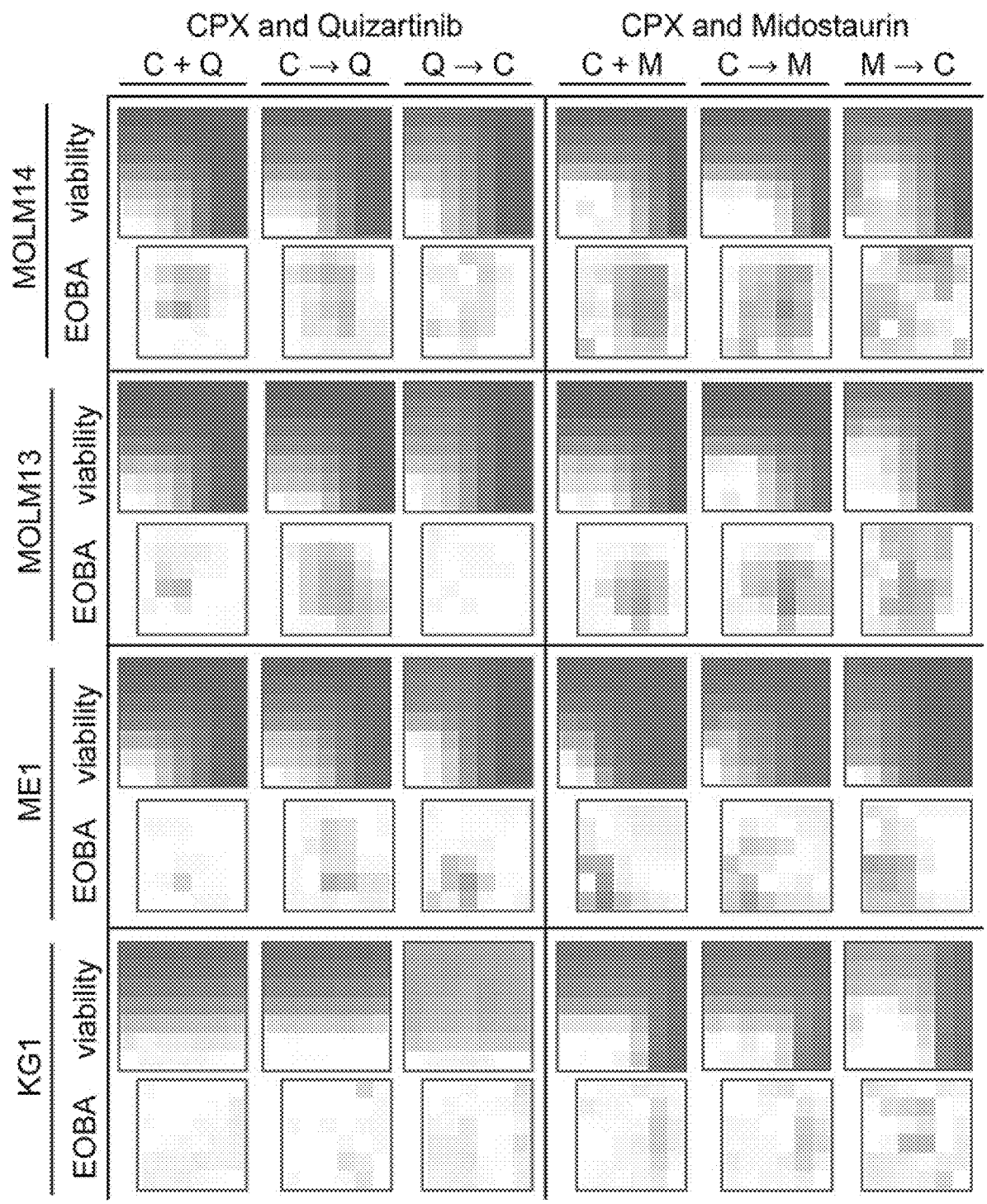

FIG. 10A shows the outline of the protocol along with numerical values of the relevant concentrations in nM of either CPX-351 or the FLT-3 inhibitor. FIG. 10B shows the results as antagonistic, additive or synergistic that would be obtained by measuring the viability of the various concentrations of the two drugs employed using the EOBA algorithm. FIG. 10C shows the experimental results on viability as a result of various concentration combinations and various protocols described above and the resulting determination of synergism based on the EOBA algorithm. Results for KG-1, ME-1, MOLM-13 and MOLM-14 are shown in FIG. 10C for the protocols set forth above. As shown, certain combinations of CPX-351 and either quizartinib or midostaurin show high synergy when administration of CPX-351 precedes administration of FLT-3 inhibitor or when they are administered simultaneously.

Figure 11A:
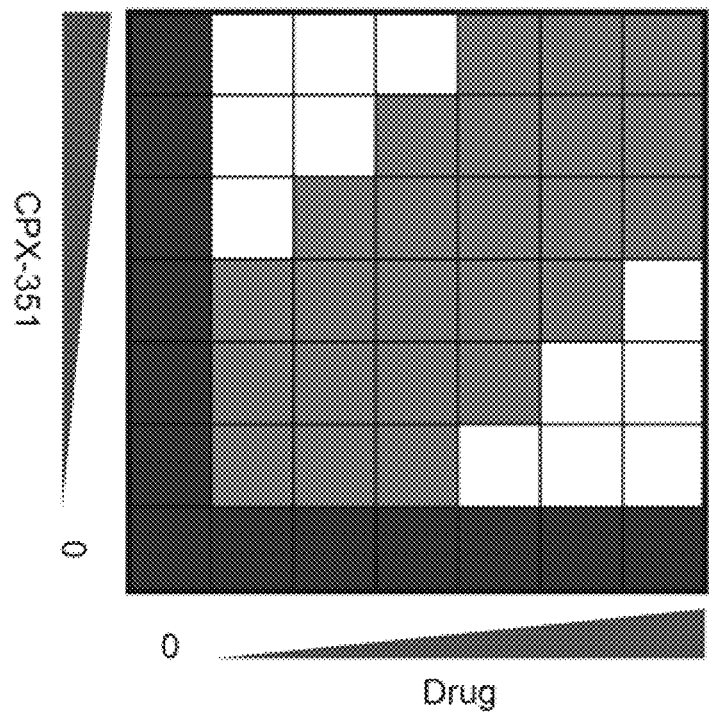
FIGS. 11A-11D show the results of determining synergy using the Chou-Talalay algorithm (Chou and Talalay, Adv. Enzyme Reg. (1984) 22:27-55).
Figure 11B:
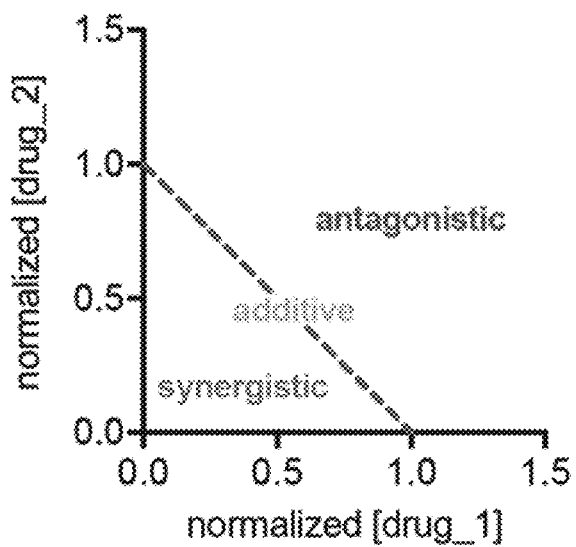
Figure 11C:
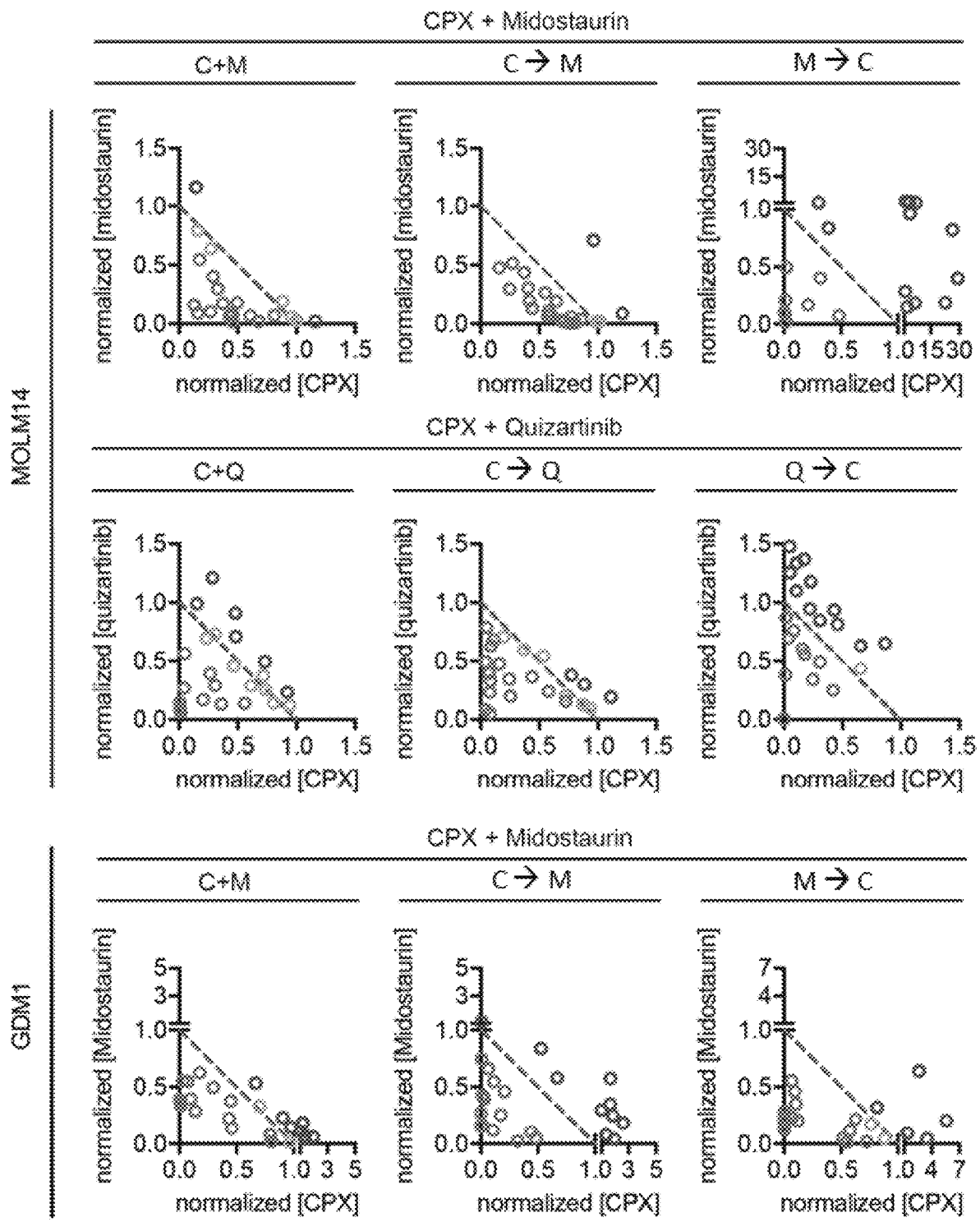
Figure 11D:
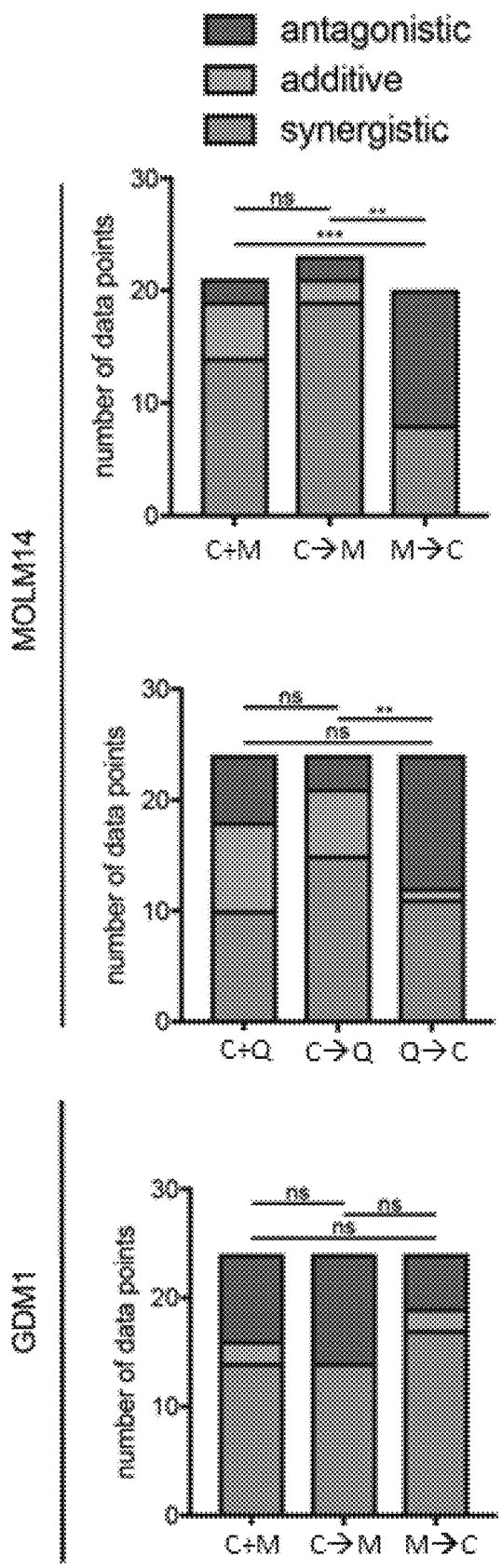

D. An alternative method of determining synergy was also employed where various combinations of FLT-3 inhibitors and protocols are compared in two cell lines. The experimental procedure of paragraph C was performed and in this case the Chou-Talalay algorithm was used to analyze the results. As shown in FIG. 11A, various combinations of CPX-351 and FLT-3 inhibitor were tested in wells represented by the shaded boxes. FIG. 11B shows a sample of an isobologram where the resultant of the Chou-Talalay analysis—i.e., a combination index (CI)—is plotted for each of the concentrations shown in FIG. 11A for all three of the protocols described above. FIG. 11C shows the results for GDM-1 cells and MOLM-14 cells for these three protocols and the concentration levels shown in FIG. 11A. The circles on each graph represent concentration combinations for each of the squares shown in FIG. 11A. As seen, for MOLM-14 cells, administration of CPX-351 either concomitantly with or before either quizartinib or midostaurin results in a high number of wells that show synergy whereas administration of these drugs prior to CPX-351 shows more antagonistic results. Results for GDM-1 cells were not significantly different. FIG. 11D is a series of graphs showing the number of data points that fell into various categories based on their combination index (CI) values for each of the protocols as shown in FIG. 11C.

E. In summary, cell lines containing FLT-3-ITD or an FLT-3-activating mutation were more sensitive to CPX-351 and exhibited increased CPX-351 uptake compared to cell lines with other genetic abnormalities.

Pretreatment with quizartinib for 16 hours resulted in approximately 50% of the total population of cells exhibiting decreased daunorubicin fluorescence indicating that prolonged prior exposure to FLT-3 inhibit may decrease CPX-351 uptake in this subpopulation.

However, robust synergy was observed when CPX-351 and FLT-3 inhibitors were provided simultaneously or when cells were exposed to CPX-351 24 hours prior to FLT-3 inhibitor exposure.

The invention claimed is:

1. A method to treat a hematologic cancer in a hematologic cancer-bearing subject which method consists essentially of administering an effective amount of a combination of an inhibitor of Fms-like tyrosine receptor kinase 3 (FLT 3) and a liposomal formulation comprising cytarabine and daunorubicin co-encapsulated at a synergistic molar ratio.

2. The method of claim 1, wherein said subject has a mutation in the Fms-like tyrosine receptor kinase 3 (FLT 3) gene.

3. The method of claim 1, wherein the mutation is an activating mutation in the FLT 3 gene.

4. The method of claim 1, wherein the FLT-3 inhibitor and the liposomal formulation are administered simultaneously or wherein the liposomal formulation is administered prior to treatment with FLT-3 inhibitor or wherein the FLT-3 inhibitor and the liposomal formulation are administered in the same composition.

5. The method of claim 1, wherein the hematologic cancer is selected from the group consisting of acute myelogenous leukemia (AML), acute lymphocytic leukemia (ALL), chronic lymphocytic leukemia (CLL), chronic myeloid leukemia (CIVIL), myeloproliferative neoplasms (MPNs) and lymphomas.

6. The method of claim 1, wherein the FLT-3 inhibitor is quizartinib, midostaurin, tandutinib, sorafenib, sunitinib, lestaurtinib, crenolanib, gilteritinib, AST-487, dovitinib or linifanib.

7. The method of claim 1, wherein the liposomal formulation is a low-cholesterol liposomal formulation.

8. The method of claim 1, wherein the liposomal formulation comprises cytarabine and daunorubicin co-encapsulated at a 5:1 molar ratio.

* * * * *